(12) United States Patent
Dimov et al.

(10) Patent No.: US 12,105,108 B2
(45) Date of Patent: Oct. 1, 2024

(54) SCALABLE BIO-ELEMENT ANALYSIS

(71) Applicant: The Board of Trustees of the Leland Stanford Junior University, Stanford, CA (US)

(72) Inventors: Ivan K. Dimov, Union City, CA (US); Thomas M. Baer, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 923 days.

(21) Appl. No.: 17/033,931

(22) Filed: Sep. 28, 2020

(65) Prior Publication Data

US 2021/0263061 A1 Aug. 26, 2021

Related U.S. Application Data

(60) Division of application No. 15/491,611, filed on Apr. 19, 2017, now Pat. No. 10,788,506, which is a
(Continued)

(51) Int. Cl.
*G01N 35/10* (2006.01)
*B82Y 15/00* (2011.01)
(Continued)

(52) U.S. Cl.
CPC ..... *G01N 35/1095* (2013.01); *C12N 15/1065* (2013.01); *G01N 33/53* (2013.01);
(Continued)

(58) Field of Classification Search
CPC .... B82Y 15/00; C12N 15/1065; G01N 33/53; G01N 33/5308; G01N 33/533;
(Continued)

(56) References Cited

U.S. PATENT DOCUMENTS

| | | |
|---|---|---|
| 4,115,535 A | 9/1978 | Giaever |
| 4,731,337 A | 3/1988 | Luotola et al. |

(Continued)

FOREIGN PATENT DOCUMENTS

| | | |
|---|---|---|
| CN | 1030139 A | 1/1989 |
| CN | 1032399 A | 4/1989 |

(Continued)

OTHER PUBLICATIONS

U.S. Appl. No. 16/903,103 Office Action dated Jan. 11, 2022.
(Continued)

*Primary Examiner* — Jeremy C Flinders
(74) *Attorney, Agent, or Firm* — McDonnell Boehnen Hulbert & Berghoff LLP

(57) ABSTRACT

A method is provided for detecting one or more analytes in a sample. The method relies, in part, on the ability of functionalized particles added to the sample to partially or completely inhibit the transmission of electromagnetic radiation into and out of the sample through a detection surface in a reaction vessel containing the sample. In a microarray format, the invention can be used to screen millions, billions or more biological elements, such as an organism, cell, protein, nucleic acid, lipid, saccharide, metabolite, or small molecules. Methods, apparatuses and kits are described.

18 Claims, 10 Drawing Sheets

Related U.S. Application Data continuation of application No. 13/791,967, filed on Mar. 9, 2013, now Pat. No. 9,657,290.

(60) Provisional application No. 61/667,930, filed on Jul. 3, 2012.

(51) Int. Cl.
| | |
|---|---|
| *C12N 15/10* | (2006.01) |
| *G01N 21/64* | (2006.01) |
| *G01N 33/53* | (2006.01) |
| *G01N 33/533* | (2006.01) |
| *G01N 33/543* | (2006.01) |
| *G01N 33/58* | (2006.01) |
| G01N 1/00 | (2006.01) |
| G01N 15/00 | (2024.01) |

(52) U.S. Cl.
CPC ....... *G01N 33/5308* (2013.01); *G01N 33/533* (2013.01); *G01N 33/54313* (2013.01); *G01N 33/54373* (2013.01); *G01N 33/582* (2013.01); *G01N 33/588* (2013.01); *B82Y 15/00* (2013.01); *G01N 2001/002* (2013.01); *G01N 2015/0011* (2013.01); *G01N 21/6428* (2013.01)

(58) Field of Classification Search
CPC ....... G01N 33/54313; G01N 33/54326; G01N 33/54373; G01N 33/582; G01N 33/588; G01N 35/1095; G01N 2001/002; G01N 2015/0011

See application file for complete search history.

(56) References Cited

U.S. PATENT DOCUMENTS

| | | | |
|---|---|---|---|
| 4,756,427 A | 7/1988 | Gohde et al. |
| 4,758,523 A | 7/1988 | Harjunmaa |
| 4,777,145 A | 10/1988 | Luotola et al. |
| 5,351,332 A | 9/1994 | Cook |
| 5,538,848 A | 7/1996 | Livak et al. |
| 5,639,606 A | 6/1997 | Willey |
| 5,643,765 A | 7/1997 | Willey |
| 5,846,717 A | 12/1998 | Brow et al. |
| 5,876,978 A | 3/1999 | Willey et al. |
| 5,962,223 A | 10/1999 | Whiteley et al. |
| 5,985,557 A | 11/1999 | Prudent et al. |
| 5,994,069 A | 11/1999 | Hall et al. |
| 6,001,567 A | 12/1999 | Brow et al. |
| 6,023,540 A | 2/2000 | Walt et al. |
| 6,027,873 A | 2/2000 | Schellenberger et al. |
| 6,090,543 A | 7/2000 | Prudent et al. |
| 6,133,436 A | 10/2000 | Koester et al. |
| 6,482,652 B2 | 11/2002 | Furlong et al. |
| 6,716,629 B2 | 4/2004 | Hess et al. |
| 6,794,127 B1 | 9/2004 | Lafferty et al. |
| 6,838,056 B2 | 1/2005 | Foster |
| 6,866,824 B2 | 3/2005 | Lafferty et al. |
| 6,964,872 B2 | 11/2005 | Sakurai et al. |
| 7,122,384 B2 | 10/2006 | Prober et al. |
| 7,157,274 B2 | 1/2007 | Bohm et al. |
| 7,264,972 B2 | 9/2007 | Foster |
| 7,572,640 B2 | 8/2009 | Goix et al. |
| 8,460,878 B2 | 6/2013 | Rissin et al. |
| 8,460,879 B2 | 6/2013 | Rissin et al. |
| 8,492,098 B2 | 7/2013 | Rissin et al. |
| 8,632,768 B2 | 1/2014 | Ildstad et al. |
| 9,314,764 B2 | 4/2016 | Hess et al. |
| 9,395,359 B2 | 7/2016 | Walt et al. |
| 9,452,184 B2 | 9/2016 | Ildstad et al. |
| 9,523,076 B2 | 12/2016 | Schoenbrunn et al. |
| 9,643,180 B2 | 5/2017 | Abrams et al. |
| 9,657,290 B2 | 5/2017 | Dimov et al. |
| 9,658,219 B2 | 5/2017 | Verschuren et al. |
| 9,746,457 B2 | 8/2017 | Hare et al. |
| 10,350,595 B2 | 7/2019 | Dimov et al. |
| 10,370,653 B2 | 8/2019 | Cochran et al. |
| 10,526,600 B2 | 1/2020 | Baer et al. |
| 10,722,885 B2 | 7/2020 | Dimov et al. |
| 10,788,506 B2 | 9/2020 | Dimov et al. |
| 2002/0045270 A1 | 4/2002 | Schurenberg et al. |
| 2002/0094533 A1 | 7/2002 | Hess et al. |
| 2002/0155439 A1 | 10/2002 | Rodriguez et al. |
| 2002/0176804 A1 | 11/2002 | Strand et al. |
| 2003/0096220 A1 | 5/2003 | Lafferty et al. |
| 2003/0124516 A1 | 7/2003 | Chung et al. |
| 2003/0153085 A1 | 8/2003 | Leary et al. |
| 2003/0156993 A1 | 8/2003 | Staats |
| 2003/0224531 A1 | 12/2003 | Brennen et al. |
| 2005/0009101 A1 | 1/2005 | Blackburn |
| 2005/0196376 A1 | 9/2005 | Loomis |
| 2006/0078998 A1 | 4/2006 | Puskas et al. |
| 2007/0259448 A1 | 11/2007 | Rissin et al. |
| 2008/0032401 A1 | 2/2008 | Edinger et al. |
| 2008/0280285 A1 | 11/2008 | Chen et al. |
| 2010/0300559 A1 | 12/2010 | Schultz et al. |
| 2010/0303687 A1 | 12/2010 | Blaga, I et al. |
| 2011/0003324 A1 | 1/2011 | Durack |
| 2011/0294139 A1 | 12/2011 | Takeda |
| 2011/0298883 A1 | 12/2011 | Ohyama |
| 2011/0311978 A1 | 12/2011 | Makarewicz, Jr. et al. |
| 2012/0122149 A1 | 5/2012 | Kocagoz |
| 2014/0011690 A1 | 1/2014 | Dimov et al. |
| 2014/0273207 A1 | 9/2014 | Chan et al. |
| 2014/0295421 A1 | 10/2014 | Link et al. |
| 2014/0345364 A1 | 11/2014 | Lin et al. |
| 2015/0011406 A1 | 1/2015 | Rich et al. |
| 2015/0038368 A1 | 2/2015 | Liu et al. |
| 2016/0040123 A1 | 2/2016 | Kanemura et al. |
| 2016/0129443 A1 | 5/2016 | Tovar et al. |
| 2016/0199834 A1 | 7/2016 | Bransky et al. |
| 2016/0215324 A1 | 7/2016 | Srinivasan et al. |
| 2016/0244749 A1 | 8/2016 | Cochran et al. |
| 2016/0245805 A1 | 8/2016 | Baer et al. |
| 2016/0281061 A1 | 9/2016 | Beachley et al. |
| 2016/0303564 A1 | 10/2016 | Gilbert et al. |
| 2017/0000825 A1 | 1/2017 | Ildstad et al. |
| 2017/0246277 A1 | 8/2017 | Schneck et al. |
| 2017/0292915 A1 | 10/2017 | Dimov et al. |
| 2018/0298324 A1 | 10/2018 | Takeda et al. |
| 2018/0353960 A1 | 12/2018 | Dimov et al. |
| 2019/0212332 A1 | 7/2019 | Dimov et al. |
| 2020/0061612 A1 | 2/2020 | Dimov et al. |
| 2020/0318104 A1 | 10/2020 | Baer et al. |
| 2021/0016277 A1 | 1/2021 | Dimov et al. |

FOREIGN PATENT DOCUMENTS

| | | |
|---|---|---|
| CN | 1360638 A | 7/2002 |
| CN | 1491359 A | 4/2004 |
| CN | 1578688 A | 2/2005 |
| CN | 101883637 A | 11/2010 |
| CN | 102224260 A | 10/2011 |
| CN | 103389287 A | 11/2013 |
| CN | 104862273 A | 8/2015 |
| CN | 108700590 A | 10/2018 |
| EP | 0177813 A1 | 4/1986 |
| EP | 2163640 B1 | 12/2011 |
| EP | 2306191 B1 | 12/2012 |
| EP | 2606120 B1 | 10/2015 |
| EP | 3037522 A1 | 6/2016 |
| JP | H0750113 B2 | 5/1995 |
| JP | 2004510996 A | 4/2004 |
| JP | 2009115473 A | 5/2009 |
| JP | 2010512534 A | 4/2010 |
| WO | WO-1986004684 | 8/1986 |
| WO | WO-1987007386 | 12/1987 |
| WO | WO-2000063404 | 10/2000 |
| WO | WO-2001038583 | 5/2001 |
| WO | WO-2002031203 | 4/2002 |
| WO | WO-2004004637 A2 | 1/2004 |
| WO | WO-2004044232 A1 | 5/2004 |
| WO | 2005022147 A1 | 3/2005 |
| WO | WO-2006110098 A1 | 10/2006 |

(56) References Cited

FOREIGN PATENT DOCUMENTS

| WO | WO-2007035586 A2 | 3/2007 |
|---|---|---|
| WO | WO-2007098148 A2 | 8/2007 |
| WO | WO-2010036827 A1 | 4/2010 |
| WO | WO-2012007537 A1 | 1/2012 |
| WO | WO-2013086783 A1 | 6/2013 |
| WO | WO-2014008056 | 1/2014 |
| WO | 2014023761 A1 | 2/2014 |
| WO | WO-2015168026 A2 | 11/2015 |
| WO | WO-2016034564 A1 | 3/2016 |
| WO | WO-2016133907 A1 | 8/2016 |
| WO | WO-2016134370 A1 | 8/2016 |
| WO | WO-2018053485 A1 | 3/2018 |
| WO | WO-2018058249 A1 | 4/2018 |
| WO | WO-2018089953 A1 | 5/2018 |
| WO | WO-2019113499 A1 | 6/2019 |

OTHER PUBLICATIONS

Pearce, E.C. et al. High precision real time metric processing for the Moss and Linear systems. Proceedings of the 2000 Space Control Conference. (2000): 145-157.

U.S. Appl. No. 16/334,353 Office Action Jun. 7, 2022.

U.S. Appl. No. 16/903,103 Notice of Allowance dated Jun. 13, 2022.

Ai et al. Engineering and characterizing monomeric fluorescent proteins for live-cell imaging applications. Nat Protoc 9:910-28 (2014).

Alberstein et al. Removing allosteric feedback inhibition of tomato 4-coumarate:CoA ligase by directed evolution. Plant J 69:57-69 (2012).

Alford et al. A Fluorogenic Red Fluorescent Protein Heterodimer. Chem Biol 19:353-60 (2012).

Alford et al. Dimerization-Dependent Green and Yellow Fluorescent Proteins. ACS Synth Biol 1:569-575 (2012).

Anderson et al., "Memory CD4+ T cells do not induce graft-versus-host disease," The Journal of Clinical Investigation 112(1):101-108, 2003.

Andersson et al. Micromachined flow-through filter-chamber for chemical reactions on beads. Sensors and Actuators 37:203-208 (2000).

Andrews et al. Probing the Origins of Catalytic Discrimination between Phosphate and Sulfate Monoester Hydrolysis: Comparative Analysis of Alkaline Phosphatase and Protein Tyrosine Phosphatases. Biochemistry 53:6811-6819 (2014).

Baker, et al. Rapid monitoring of recombinant protein products: a comparison of current technologies. Trends Biotechnol. Apr. 2002;20(4):149-56.

Bao et al. A microfluidic device for physical trapping and electrical lysis of bacterial cells. Applied Physics Letters 92:1-2(2008).

Brune et al. Direct, Real-Time Measurement of Rapid Inorganic Phosphate Release Using a Novel Fluorescent Probe and Its Application to Actomyosin Subfragment 1 ATPase. Biochemistry 33:8262-8271 (1994).

Chalfie, et al. Green fluorescent protein as a marker for gene expression. Science 1994. 263(5148):802-805.

Chao et al. Isolating and engineering human antibodies using yeast surface display. Nature protocols 1:755-768 (2006).

Chen et al., "High-throughput analysis and protein engineering using microcapillary arrays," Nature Chemical Biology 12:76-81, 2016. Published Dec. 7, 2015. (9 pages).

Clinical Trials.gov. 2009. Datasheet [online].Selective depletion of CD45RA+ T cells from allogeneic peripheral blood stem cell grafts for the prevention of GVHD. NIH.NLM. Identifier: NCT00914940. Retrieved Dec. 26, 2019. Downloaded from the internet: https://clinicaltrials.gov/ct2/show/NCT00914940 pp. 1-11; 1,2.

De Freitas et al. Pulsatile dynamic stiffness of cartilage Dlike materials and use of agarose gels to validate mechanical methods and models. 78B(2):347-357 (2006).

De Loor, et al. Polygon Laser Scanning. Laser Technik Journal 11 (2014): 32-34.

EP13813011.7 Extended European Search Report dated Jun. 24, 2016.

EP16753225.8 Extended European Search Report dated Jun. 21, 2018.

EP17851769.4 The Extended European Search Report dated Apr. 21, 2020.

EP17870339.3 The Extended European Search Report dated Apr. 24, 2020.

EP18184686.6 The Extended European Search Report dated May 9, 2019.

EP18184686.6 The Partial European Search Report dated Feb. 6, 2019.

Fischlechner et al. Evolution of enzyme catalysts caged in biomimetic gel-shell beads. Nat Chem 6:791-796 (2014).

Fitzgerald et al. Exploiting Highly Ordered Subnanoliter Volume Microcapillaries as Microtools for the Analysis of Antibody Producing Cells. Anal Chem 87:997-1003 (2015). Published Dec. 5, 2014.

Galajda et al. A Wall of Funnels Concentrates Swimming Bacteria. Journal of Bacteriology 189:8704-8707 (2007).

Griss, et al. Expandable microspheres for the handling of liquids. Lab Chip. May 2002;2(2):117-20. Epub Feb. 27, 2002.

Groisman et al. A microfluidic chemostat for experiments with bacterial and yeast cells. Nature Methods 2:685-689 (2005).

Heim et al. Improved green fluorescence. Nature 373:663-664 (1995).

Hu et al. Engineering of a fungal β-galactosidase to remove product inhibition by galactose. Appl Microbiol Biotechnol 87:1773-1782 (2010).

Huft et al. Three-dimensional large-scale microfluidic integration by laser ablation of interlayer connections. Lab Chip 10:2358-2365 (2010).

Huse et al. Application of a Filamentous Phage pVIII Fusion Protein System Suitable for Efficient Production, Screening and Mutagenesis of F(ab) Antibody Fragments. J. Immunol 149:3914-3920 (1992).

Kariolis et al.An engineered Axl 'decoy receptor' effectively silences the Gas6/Axl signaling axis Nat Chem Biol 10:977-983 (2014).

Kielberg et al. Tech Note No. 14 from Cryopreservation of Mammalian Cells, Thermo Scientific (2010).

Laurell et al. Chip integrated strategies for acoustic separation and manipulation of cells and particles. Chem. Soc. Rev. 36:492-506 (2007).

Lim et al. Bead-based microfluidic immunoassays: The next generation. Biosensors and Bioelectronics 22:1197-1204 (2007).

Mandal et al. Encapsulation of Magnetic and Fluorescent Nanoparticles in Emulsion Droplets. Langmuir 21:4175-4179 (2005).

Miraglia, et al. Homogeneous Cell- and Bead-Based Assays for High Throughput Screening Using Fluorometric Microvolume Assay Technology. 1999, J. of Biomol. Screen. 4: 193-204.

Murakami et al. On-chip micro-flow polystyrene Bead-based immunoassay for quantitative detection of tacrolimus (FK506). Analytical Biochemistry 334:111-116.

O'Brien et al. Functional Interrelationships in the Alkaline Phosphatase Superfamily: Phosphodiesterase Activity of *Escherichia coli* Alkaline Phosphatase. Biochemistry 40:5691-5699 (2001).

PCT/US2013/047792 International Search Report dated Jan. 16, 2014.

PCT/US2016/018954 International Search Report dated Jun. 24, 2016.

PCT/US2017/052218 International Search Report dated Dec. 5, 2017.

PCT/US2017/061414 International Search Report dated Mar. 8, 2018.

Rajan et al. The living microarray: a high-throughput platform for measuring transcription dynamics in single cells. BMC genomics vol. 12:115 Feb. 16, 2011, doi:10.1186/1471-2164-12-115.

Shaner et al. Improved monomeric red, orange and yellow fluorescent proteins derived from *Discosoma* sp. red fluorescent protein. Nat Biotechnol. 22:1567-1572 (2014).

(56) References Cited

OTHER PUBLICATIONS

Shields, et al. Microfluidic cell sorting: a review of the advances in the separation of cells from debulking to rare cell isolation. Lab on a Chip 15.5 (2015): 1230-1249. doi:10.1039/c4lc01246a.

Steinberg et al. Early Keratinocyte Differentiation on Micropillar Interfaces.Nano Letters 7(2):287-294 (2007).

Thompson et al. Polymeric microbead arrays for microfluidic applications. J Micromech Microeng 20:1-8 (2010).

U.S. Appl. No. 13/791,967 Notice of Allowance dated Feb. 13, 2017.

U.S. Appl. No. 13/791,967 Notice of Allowance dated Jan. 10, 2017.

U.S. Appl. No. 13/791,967 Office Action dated Dec. 9, 2015.

U.S. Appl. No. 13/791,967 Office Action dated May 24, 2016.

U.S. Appl. No. 15/491,611 Notice of Allowance dated May 21, 2020.

U.S. Appl. No. 16/334,353 Final Office Action dated Oct. 13, 2021.

U.S. Appl. No. 16/334,353 Office Action dated Mar. 25, 2021.

U.S. Appl. No. 16/334,353 Office Action dated May 7, 2020.

U.S. Appl. No. 16/425,856 Notice of Allowance dated May 28, 2020.

U.S. Appl. No. 15/050,130 Notice of Allowance dated Aug. 19, 2019.

U.S. Appl. No. 15/050,130 Office Action dated Jun. 11, 2018.

U.S. Appl. No. 15/050,130 Office Action dated Mar. 26, 2019.

U.S. Appl. No. 15/050,130 Office Action dated Nov. 1, 2017.

U.S. Appl. No. 15/050,142 Notice of Allowance Mar. 20, 2019.

U.S. Appl. No. 15/050,142 Office Action dated Dec. 14, 2017.

U.S. Appl. No. 15/050,142 Office Action dated May 15, 2018.

U.S. Appl. No. 15/491,611 Office Action dated Nov. 21, 2019.

U.S. Appl. No. 16/044,166 Notice of Allowance dated Apr. 17, 2019.

U.S. Appl. No. 16/044,166 Office Action dated Dec. 21, 2018.

U.S. Appl. No. 16/334,353 Office Action dated Dec. 31, 2019.

U.S. Appl. No. 16/425,856 Office Action dated Dec. 18, 2019.

Van Deventer, et al., Yeast Surface Display for Antibody Isolation: Library Construction, Library Screening, and Affinity Maturation, Monoclonal Antibodies: Methods and Protocols, Methods in Molecular Biology, Springer Science, Business Media New York 2014 1131:151-81.

Wolf et al. Quantitative Analysis of Digital Microscope Images. Methods Cell Biol 114:337-367 (2007).

Xia et al. Combined microfluidic-micromagnetic separation of living cells in continuous flow. Biomed Microdevices 8:299-308 (2006).

Yang et al. Rational Engineering of Enzyme Allosteric Regulation through Sequence Evolution Analysis. PLOS Comput Biol 8:e1002612 (2012).

Zaytseva et al. Development of a microfluidic biosensor module for pathogen detection. Lab Chip 5:805-811 (2005).

Zinchenko et al. One in a Million: Flow Cytometric Sorting of Single Cell-Lysate Assays in Monodisperse Picolitre Double Emulsion Droplets for Directed Evolution. Anal. Chem. 86:2526-2533 (2014).

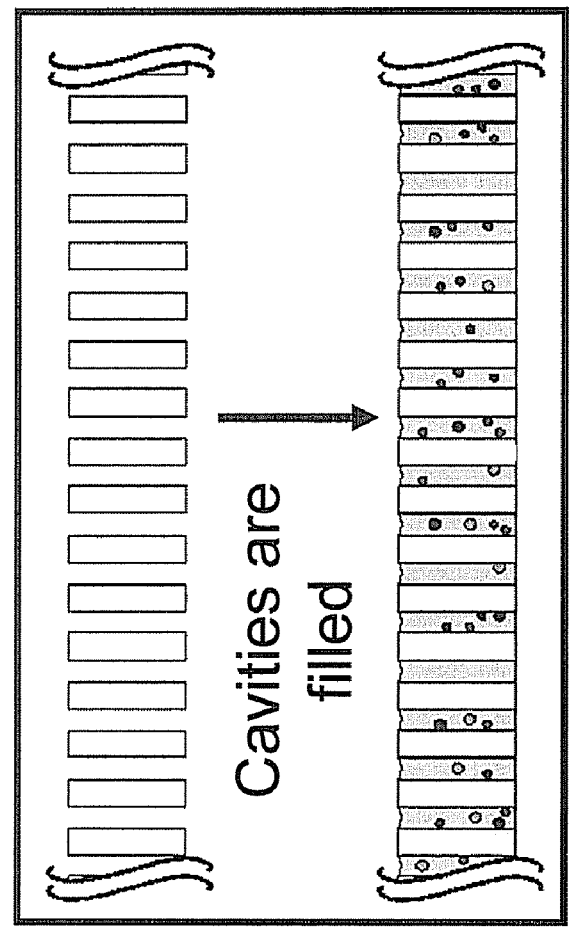
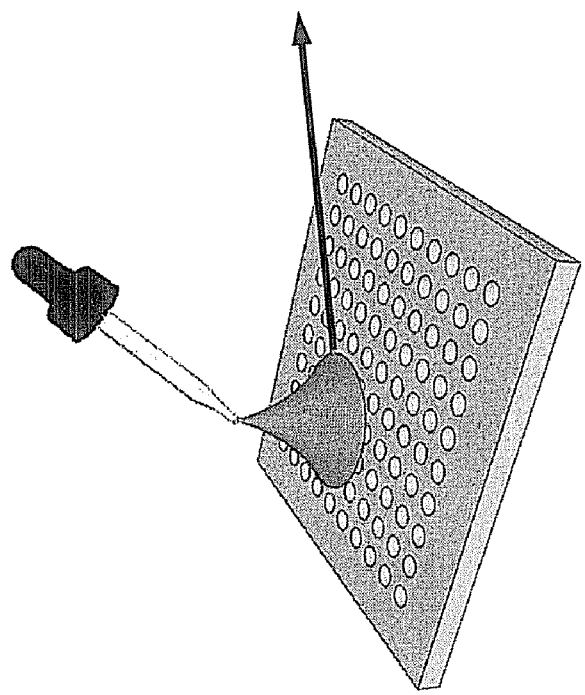
Figure 3

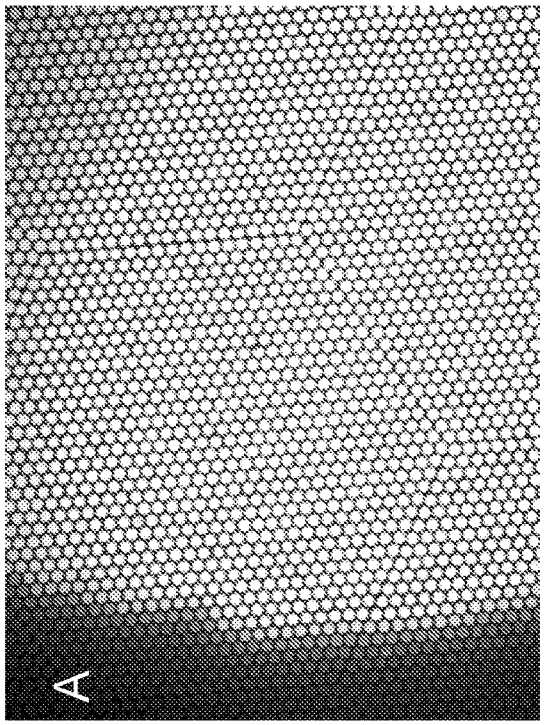
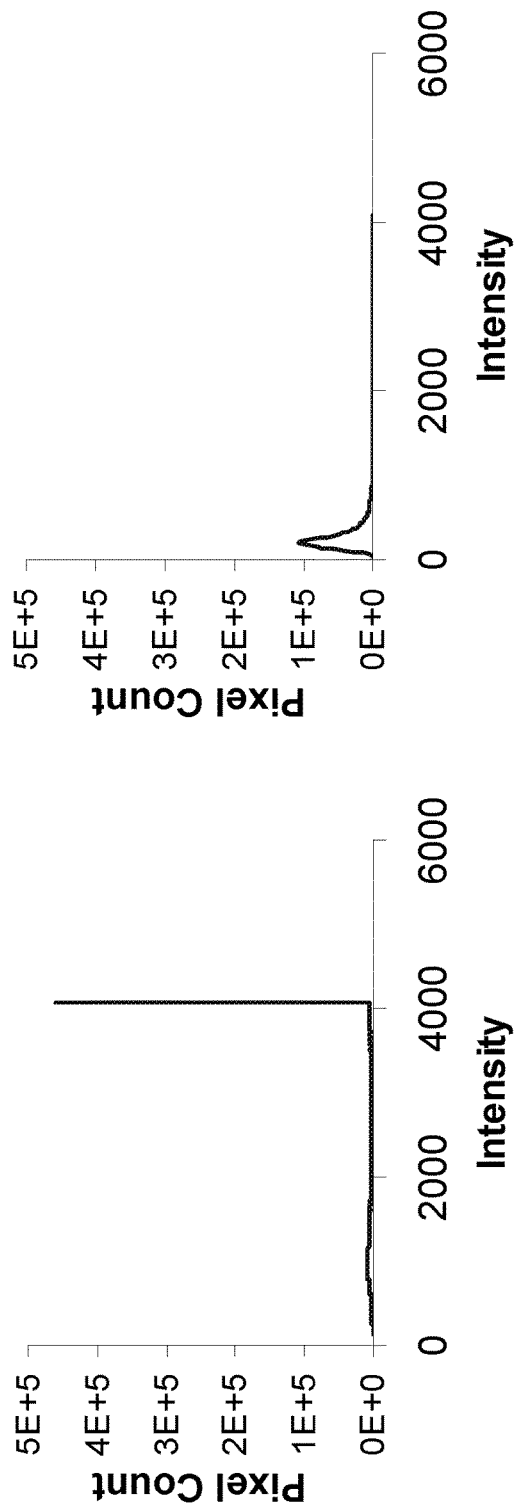
Figure 5

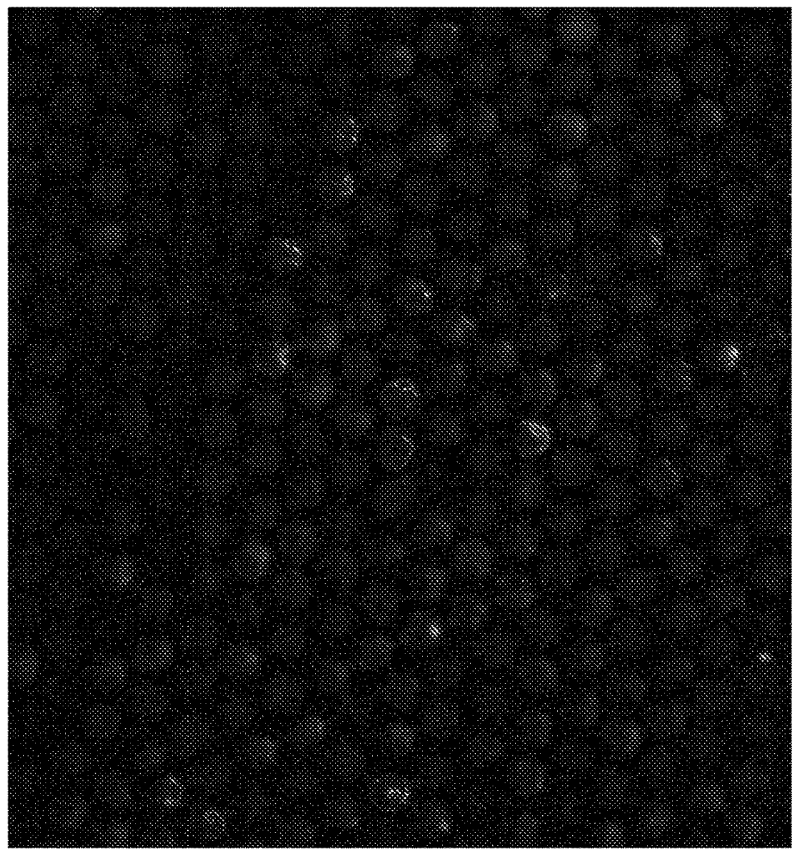
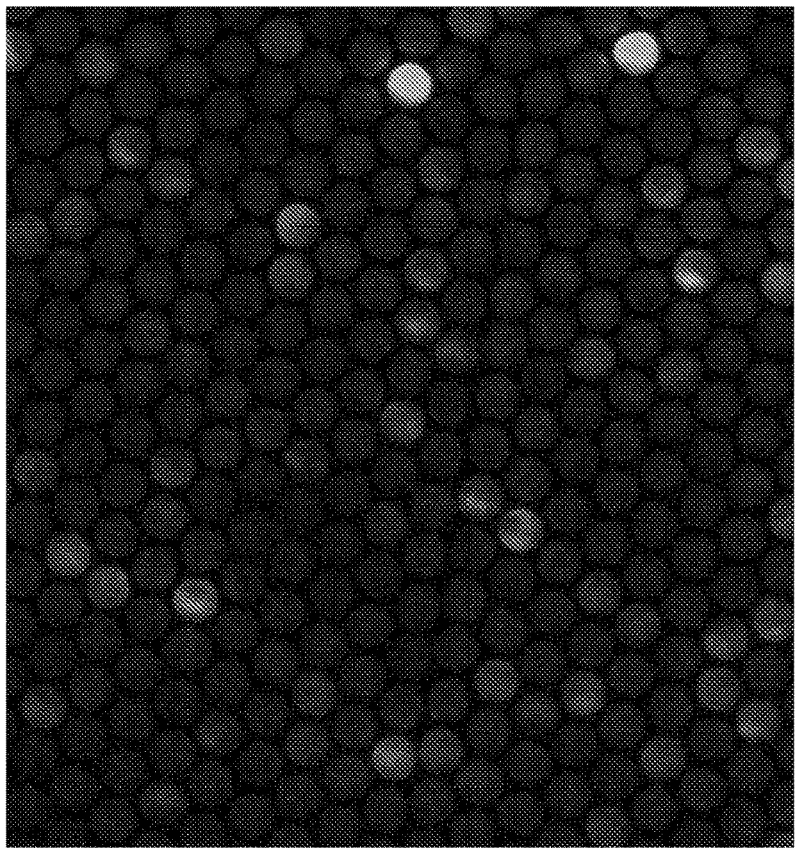
Figure 7

SCALABLE BIO-ELEMENT ANALYSIS

CROSS REFERENCE TO RELATED APPLICATION

This application is a divisional of U.S. patent application Ser. No. 15/491,611 filed Apr. 19, 2017, which is a continuation of U.S. patent application Ser. No. 13/791,967 filed Mar. 9, 2013, which claims the benefit of U.S. Provisional Patent Application Ser. No. 61/667,930 filed Jul. 3, 2012, these applications being incorporated by reference herein in their entirety.

BACKGROUND

Technical Field

The invention relates to the detection of one or more analytes in a sample or a series of samples. More particularly, the invention relates to a method for determining one or more biological elements, e.g., biological cells, in a population of biological elements.

Related Art

Using conventional technologies, biological libraries may be screened for components containing, for example, cells, antibodies, proteins, peptides and, nucleic acids. These technologies include phage display, ribosome display, yeast, bacterial display, in vitro compartmentalization, microengraving and spatial addressing. Such systems have a number of disadvantages, including the need to enrich for desired clones via repeat selection steps (including, for example "panning") that inherently result in the loss of potential binding candidates. It is also difficult to establish the precise origin of a positive signal using conventional technologies since they obtain mixed signals from heterogeneous populations that cannot be deconvoluted. Generally these techniques involve selection processes utilizing bacteriophages, ribosomes and specific cells, most of which are performed in vitro.

Improvements in library screening have introduced the concept of spatial addressing in order to maintain identity of the screened components during the selection process. Such addressing can be based upon techniques including robotics, enzyme-linked immunosorbent assays, or cell-based assays. While spatial addressing can, for example, identify specific cellular clones to generate master stocks, these approaches do not facilitate high throughput screening techniques to selectively isolate and purify the identified clones for rapid application to disease diagnostics and therapeutics. Another disadvantage of the present screening assays is that they are usually limited to a cell number between approximately 50 and 100 thousand.

For performing cell-based screening, one of the particular challenges is the isolation of small populations of cells in a manner that allows for subsequent screening procedures. Traditional devices and methods of isolating cells do not adequately provide for the isolation of small populations of cells without performing steps that potentially modify cellular function or activity. Isolation of cells is not only important in screening, but also in processes that involve the monitoring, measuring, and/or use of the output of cellular activity or function (e.g., antibody production) for small populations of cells.

Accordingly, the need to isolate small numbers of specific cells from background populations is ubiquitous, with applications in pathology, clinical diagnosis, cloning, and cell biology research. Current screening methods have numerous technical challenges, including: the size of protein displayed has to be small, the multiplicity of infection (MOI) needs to be high to avoid loss of diversity, the dependency on the activity of the phage, multiple panning rounds are needed (taking up to 1 week or more), high non-specific binding due to phage, antibodies may not function well in soluble form (truncated clones are often expressed), and/or avidity effects can hinder selection of high affinity clones.

Accordingly, the inventors have identified a need in the art for a more efficient process of identifying, isolating and characterizing components of biological populations.

SUMMARY

In one aspect, the invention is directed to a method for detecting an analyte in a sample. The method relies, in part, on the ability of microparticles in a sample to partially or completely inhibit the transmission of electromagnetic radiation into and out of the sample through a detection surface in a vessel containing the sample. In one embodiment, the method includes adding to a reaction vessel containing a sample solution, first particles, and a first label that emits electromagnetic radiation, wherein the first label is bound to the first particles or the first label becomes bound to the first particles as a result of the presence or absence of the analyte in the sample. The first particles are accumulated at a first detection surface to inhibit the transmission of electromagnetic radiation into and out of the sample through the surface. The presence or amount of electromagnetic radiation emitted from the first detection surface is detected. The first particles may accumulate at the detection surface as a result of a force applied to the sample, wherein the force is selected from gravitational, magnetic, electrical, centrifugal, convective and acoustic forces. In one aspect, the label is bound to the particle and is released as a result of the presence or absence of the analyte in the sample.

In a further embodiment, the method of the invention includes adding to the vessel a second label that emits electromagnetic radiation and second particles that are different from the first particles based upon at least shape, size, density, magnetic permittivity, charge, and optical coating, wherein the second label is bound to the second particles or the second label becomes bound to the second particles as a result of the presence or absence of a second analyte in the sample. The second particles are accumulated at a second detection surface to inhibit the transmission of electromagnetic radiation into and out of the sample through the second detection surface. The presence or amount of electromagnetic radiation emitted at the second detection surface is detected. In various aspects of this embodiment, the first particles accumulate at the first detection surface as a result of a first force and the second particles accumulate at the second detection surface as a result of second force, wherein the first force and the second force are independently selected from gravitational, magnetic, electrical, centrifugal, convective and acoustic forces, and wherein the first force and the second force are applied to the sample either simultaneously or sequentially. Alternatively, the second particles may be accumulated at the first detection surface to inhibit the transmission of electromagnetic radiation into and out of the sample through the first detection surface, wherein the first particles accumulate at the first detection surface as a result of a first force and the second particles accumulate at the first detection surface as a result of second force, wherein the first force and the second force are independently selected from gravitational, magnetic, electrical, centrifugal, convective and acoustic forces, and wherein the first force and the second force are applied to the sample sequentially. The presence or amount of electromagnetic radiation emitted from the first particles and the second particles can be detected at the first detection surface.

Still further, the invention is directed to a method for detecting a target biological element from a heterogeneous population of biological elements The method includes distributing the heterogeneous population of biological elements into an array of receptacles; adding to the array particles and a first label that emits electromagnetic radiation upon activation, wherein the first label is bound to the first particles or the first label becomes bound to the first particles as a result of the presence or absence of the analyte in the sample; applying a force to the array to accumulate the particles at a surface of the sample in each of the receptacles; and identifying the presence or amounts of electromagnetic radiation emitted by the receptacles, thereby identifying receptacles containing the target biological element. The array of receptacles may be a microcavity array having a plurality of longitudinally fused capillaries that have a diameter of about 1 to about 500 micrometers. In addition, the array may have between about 300 and 64,000,000 of the capillaries per square centimeter of the array. The sample may be added to the array at a concentration that is intended to introduce no more than a single biological element in each receptacle.

In various embodiments of the invention, the vessels or receptacles are microcavities having detection surfaces that are the meniscuses of the sample solution in the microcavities. The sample may be mixed by applying a magnetic field to move the particles within the sample solution, wherein the particles are magnetic.

In addition, the biological element may be an organism, cell, protein, nucleic acid, lipids, saccharides, metabolite, or small molecule. For instance, the cell produces a recombinant protein such as an enzyme or antibody.

Still further, the invention is directed to a method of extracting a solution including a biological element from a single microcavity associated with an electromagnetic radiation absorbent material in a microcavity array. The method includes focusing electromagnetic radiation at the microcavity to generate an expansion of the material or the sample or an evaporation of the sample that expels at least part of the sample from the microcavity. In various embodiments, material includes particles in the microcavity or the material is a high thermal expansion material at least partially coating or covering the microcavity.

BRIEF DESCRIPTION OF THE FIGURES

FIG. 3 illustrates one embodiment of adding or loading a sample solution comprising the analyte and other biological elements to an array container.

FIG. 5 illustrates the ability of the particles to inhibit the signal from labels in solution that are not bound to the particles.

FIG. 7 demonstrates the specificity of the disclosed methods at the single cell level. In this embodiment, all of the pores of the array comprise E. coli cells expressing recombinant protein GFP. Each well also contains magnetic beads coated with a rabbit anti-GFP antibody (Pos. Ctrl) and magnetic beads coated with Oligo(dT)$_{25}$ (Neg. Ctrl).

DETAILED DESCRIPTION OF THE EMBODIMENTS

Figure 1:
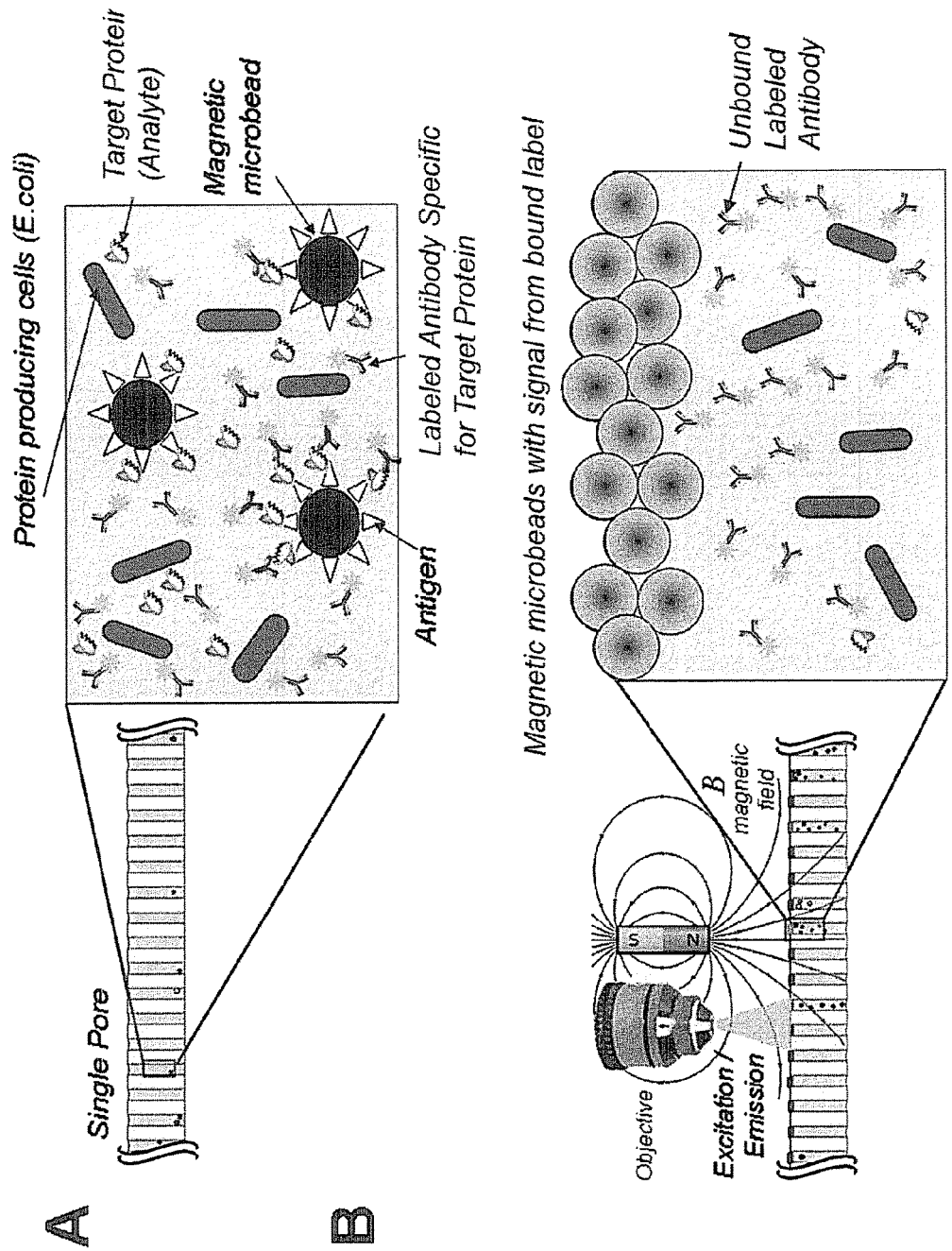
FIG. 1 is a schematic diagram of a representative embodiment of the methods disclosed herein.

The invention is directed to methods, apparatus, and kits for detecting an analyte in a sample. In various embodiments, the invention is directed to the screening of large populations of biological elements for the presence or absence of subpopulation of biological elements or a single element. The invention can be used to discover, characterize and select specific interactions from a heterogeneous population of millions or billions of biological elements.

The invention uses biological assay techniques wherein functionalized particles accumulate at a surface of a sample vessel and physically inhibit, either partially or completely, the transmission of electromagnetic radiation into and/or out of a sample liquid. In a specific embodiment, a high-density microcavity, e.g., micropore, array is screened by detecting an electromagnetic signal emitted from a label in each cavity. High sensitivity can be accomplished with an array that is arranged such that each cavity contains a single or a few biological elements and microparticles capable of inhibiting electromagnetic (EM) radiation into and/or out of each cavity. Through the use of micro-cavity arrays and a homogenous particle-based assay, the method of the invention provides for scalable single cell analysis. This method can be used to discover very rare (1 in $10^8$) biological elements, e.g., cells, in large complex mixtures.

The invention provides several advantages over other methods of screening populations of biological elements. First, it allows simple screening of millions, billions or more, of biological interactions in parallel. The invention also allows for the display and independent recovery of analytes, such as target cells. In addition, it provides concentration versus affinity information for billions of clones in parallel (e.g., feedback on production efficiency can be provided for each expressed gene).

In one embodiment, disclosed is a method for selecting a subpopulation antibody producing biological cell clones, e.g., a single or several cell clones, from a population of thousands, millions, or even billions of cell clones using a micro-cavity array (for example, a porous glass array). In one embodiment, the micro-cavity are filled with a solution (e.g., a culture media) containing biological cell clones harboring antibody (or any protein of interest) producing genes. The cells grow and express antibodies into the media, which can react and bind with a binding partner that is immobilized on a particle within the media. An antigen-antibody complex can be detected by adding fluorescent reagents (e.g., fluorescently-labeled anti-analyte antibody) to the media.

In one embodiment, the method includes recovering the biological cells from the micropore array. In one embodiment, the biological cells comprise cells producing a fluorescent protein. In one embodiment, the biological cells comprise cells producing a fluorescent protein fused to a non-fluorescent protein.

The present invention may be used to isolate any types of biological cells, including, but not limited to, cell lines that express or produce proteins, carbohydrates, enzymes, peptides, hormones, receptors; other cell lines that produce antibodies; genetically engineered cells; and activated cells. Moreover, the present invention may be used to screen for a variety of biological activities including, but not limited to, the expression of surface receptor proteins, enzyme production, and peptide production. Furthermore, the present invention may be used to screen a variety of test agents to determine the effect of the test agents on the desired biological activity. Other types of cells desired to be isolated and screened, other types of biological activity desired to be detected, and specific test agents to be screened will be readily appreciated by one of skill in the art.

Definitions

Unless otherwise defined, the technical and scientific terms used herein have the same meaning as commonly understood by one of ordinary skill in the art. Expansion and clarification of some terms are provided herein. All publications, patent applications, patents and other references mentioned herein, if not otherwise indicated, are explicitly incorporated by reference.

As used herein, the singular forms "a," "an", and "the" include plural referents unless the context clearly dictates otherwise.

The terms "binding partner", "ligand" or "receptor" as used herein, may be any of a large number of different molecules, or aggregates, and the terms are used interchangeably. In various embodiments, the binding partner may be associated with or bind an analyte being detected. Proteins, polypeptides, peptides, nucleic acids (nucleotides, oligonucleotides and polynucleotides), antibodies, saccharides, polysaccharides, lipids, receptors, test compounds (particularly those produced by combinatorial chemistry), may each be a binding partner.

The term "biological cell", refers to any cell from an organism, including, but not limited to, viral, insect, microbial, fungal (for example, yeast) or animal, (for example, mammalian) cells.

The term "biological element" as used herein, refers to any bioreactive molecule. Non-limiting examples of these molecules include proteins, nucleid acids, peptides, antibodies, antibody fragments, enzymes, hormones, biological cells, and small molecules.

An "analyte" generally refers to an element of interest in a sample, for example a biological element of interest in a biological sample.

The term "bind" or "attach" as used herein, includes any physical attachment or close association, which may be permanent or temporary. These attachments or close associations may be interactions. Non-limiting examples of these associations are hydrogen bonding, hydrophobic forces, van der Waals forces, covalent bonding, and/or ionic bonding. These interactions can facilitate physical attachment between a molecule of interest and the analyte being measured. The "binding" interaction may be brief as in the situation where binding causes a chemical reaction to occur, such as for example when the binding component is an enzyme and the analyte is a substrate for the enzyme.

Specific binding reactions resulting from contact between the binding agent and the analyte are also within this definition. Such reactions are the result of interaction of, for example, an antibody and, for example a protein or peptide, such that the interaction is dependent upon the presence of a particular structure (e.g., an antigenic determinant or epitope) on a protein. In other words an antibody is recognizing and binding to a specific protein structure rather than to proteins in general. For example, if an antibody is specific for epitope "A", the presence of a protein containing epitope A (or free, unlabelled A) in a reaction containing labeled "A" and the antibody will reduce the amount of labeled A bound to the antibody. Specific binding interactions can occur between other molecules as well, including, for example, protein-protein interactions, protein-small molecule interactions, antibody-small molecule interactions, and protein-carbohydrate interactions. Each of these interactions may occur at the surface of a cell.

The terms "arrays" and "microarrays" are used interchangeably differing only in general size. In various embodiments, the arrays typically contain a multitude (typically 100 to over 1,000,000) of distinct reaction spaces, for pores, wells, cavities, containers or receptacles, wherein each vessel can be at a known location and contain a single or numerous components of interest.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL), which comprises fluid and cells derived from lung tissues. A biological sample may comprise a cell, tissue extract, body fluid, chromosomes or extrachromosomal elements isolated from a cell, genomic DNA, RNA, cDNA and the like.

Description of Various Embodiments

Disclosed is a method for detecting an analyte in a sample. The method includes adding to a vessel having a defined detection surface a sample solution containing the analyte, particles, and a label that emits electromagnetic radiation. The particles can accumulate at the detection surface as a result of a force applied to the vessel and inhibit emission of a signal from the label in the sample other than the label that may be attached to the particles accumulated at the detection surface. The presence or absence of the analyte in the sample controls whether the particles can accumulate at a detection surface of the vessel and/or whether a label that may be bound to the particles at the surface can emit electromagnetic radiation. The invention can be used with a variety of assay formats known in the art.

In one aspect, the label is bound to the particles or the label becomes bound to the particles as a result of the presence or absence of the analyte in the sample. In accordance with this embodiment of the disclosure, the particles may be functionalized with a binding partner that binds the analyte, which can be analyzed with assay formats well known to those of skill in the art, e.g., sandwich and competitive immunoassay methods. In a sandwich method, the particle is functionalized with a binding partner for the analyte and is mixed with a label that includes a moiety capable of emitting a signal (e.g., fluorescent moiety) and a binding partner for the analyte. The label becomes bound to the particle as a result of the binding of the analyte to the particle and the label. The presence of the label on the particle indicates the presence of the analyte in the sample. In a competitive detection format, particles having a binding partner for the analyte and a label that includes second binding partner that is an analogue of the analyte are mixed with the sample. The analogue binds in competition with the analyte in the sample to the binding partner for the analyte on the particle. The absence of signal from the label indicates the presence of the analyte in the sample.

In another assay format, the analyte is an enzyme, and the particle is functionalized directly with a substrate for the enzyme (e.g., by covalent binding) that acts as a label, or the enzyme is bound to the particle as a result of specific or non-specific binding, or other interaction. The presence or absence of signal from the enzyme/label is indicative of the activity of the analyte/enzyme to convert the label from signal producing to non-signal producing, or vice versa.

Another assay format uses the analyte's ability to release a label bound to a particle. For example, the analyte may be an enzyme that cleaves a linker between the label and the particle. Alternatively, the analyte, when present in the sample may prevent cleavage of the linker and release of the label from the particle.

After the binding or enzyme reaction is allowed to proceed, the particles are accumulated at a detection surface to inhibit, either partially or completely, the transmission of electromagnetic radiation into and out of the sample through the surface. The presence or amount of electromagnetic radiation at the detection surface is then determined. Accordingly, when the particles are accumulated at the surface, electromagnetic radiation from the label attached to the particles can be detected at the surface. The particles, however, act as a shutter at the surface to inhibit electromagnetic radiation from label that is not bound the particles. Accordingly, the background signal of unbound label in the sample is eliminated. Similarly, when the particles do not have any bound label, the particles will not emit any electromagnetic radiation at the detection surface and act as a shutter to inhibit signal from unbound label in the sample solution from being detected at the surface.

In another embodiment, a reaction vessel includes a binding partner on the wall of the vessel. In a binding reaction as a result of the presence or absence of the analyte, the particles are captured, or not, on the surface of the reaction vessel. The particles do not then inhibit transmission of electromagnetic radiation from a label in the sample out of the reaction vessel through a detection surface. In this embodiment, the label is not required to participate in the binding reaction and can remain unbound in solution. The binding reaction controls the ability of the particles to accumulate at the detection surface when a force applied to the reaction vessel. In this embodiment, particles may become bound to the surface of the vessel in the presence of the analyte when the particles and the wall of the vessel are coated with binding partners for the analyte, wherein the analyte becomes sandwiched by the binding partners. In this embodiment, a signal from the label in the reaction vessel indicates the presence of the analyte because the particles become bound to wall of the reaction vessel and are unable to inhibit electromagnetic radiation from exiting the vessel. In a competitive assay format, a particle coated with an analyte analogue would bind to a vessel wall coated with a binding partner for the analyte in the absence of the analyte. Therefore the absence of a signal from the vessel would indicate the presence of the analyte.

When the label is activatable by an external source, e.g., a fluorescent label excitable by electromagnetic radiation, the particles accumulated at the surface will prevent the electromagnetic radiation from exciting any label other than label bound to particles at the surface. The particles at the detection surface act as a shutter to prevent electromagnetic radiation from entering the sample solution and exciting unbound label in solution. Accordingly, only label that is attached to the particles at the surface are excited and background signal from unbound label is avoided. When the label is activatable by a source other than electromagnetic radiation (e.g., heat, electricity, chemical reaction, enzymatic reaction), the electromagnetic radiation from activated label in the sample is prevented from exiting the vessel through the detection surface because of particles accumulated at the detection surface.

The size of the reaction vessel is limited only by the ability of the particles to accumulate at a reaction surface of the vessel and inhibit, either partially or completely, the transmission of electromagnetic radiation in to and out of the vessel. Smaller formats are preferred as smaller sample sizes are necessary for screening multitudes of biological elements in an efficient manner.

Reaction vessels suitable for use with the invention have or can be constructed to have a detection surface where the functionalized particles can be accumulated. The surface is not limited to particular material as long as it is transmissive to electromagnetic radiation. Alternatively, the surface is not bound by any material and may be open to the environment such that the detection surface is the surface of the sample solution, for instance the meniscus of the sample solution in a reaction well, microwell, micropore, capillary or microcavity. Transmission of electromagnetic radiation through the surface should be unimpeded except when the particles are accumulated at the surface. On a macroscale, the surface may be a window in a cuvette or reaction well. Regardless of vessel size, the area surrounding the surface should prevent the transmission of electromagnetic radiation in to and out of the sample such that electromagnetic radiation can enter the sample only through the surface. A reaction vessel may have more than one surface, such as, for example, multiple windows or a meniscus at each open end of a capillary or microtube.

Accumulation of particles at the detection surface can be accomplished by applying a force to the sample that draws the particles to the surface. The force should be sufficient such that the accumulation of particles prevents at least 50% of the electromagnetic radiation from passing through the accumulated particles. In particular embodiments, electromagnetic radiation is inhibited from entering or exiting the sample through the detection surface when at least 30%, 40%, 50%, 60%, 70%, 80%, 90%, 95% or 100% of the radiation is prevented from entering or exiting the sample through the surface. Exemplary types of forces that can be used to accumulate particles at the detection surface include gravitational, magnetic, electrical, centrifugal and acoustical forces.

Gravitational force can be used to allow particles to settle at the bottom of a reaction vessel. When the bottom of the vessel includes a detection surface, the signal from a label associated with the particles can be detected. Magnetic force applied to the sample containing magnetic particles can be used to draw the particles to a detection surface at the top or other location in the vessel. In specific embodiments, the magnetic force is applied by a magnet, e.g., a cubed neodymium magnet (B666, K&J Magnetics Inc.).

Similarly, charged particles can be used subjected to electrical forces that move the particles throughout the sample and towards a detection surface. In some embodiments, the force is an electrokinetic force as described, for example, in U.S. patent publication No. 2006/0078998, which is incorporated by reference herein in its entirety. In some embodiments the particles are insulating and inhibit the application of an electrical force to the sample, thereby preventing the activation of an electrically stimulated label in the sample.

Likewise, different shaped particles with different resonant frequencies can be used subjected acoustic wave frequency that displace and accumulate the resonant particles to the acoustic pressure nodes. In some embodiments, the force is an acoustic force as described in, for example, in Laurell, T., et al., Chem. Soc. Rev. 2007, 36:492-506, which is incorporated by reference herein in its entirety.

FIG. 1 depicts an exemplary antigen-antibody recognition assay, or "sandwich" assay in a micropore array. In this embodiment, the particles are magnetic microparticles and are associated with and/or bound to the antigen. The analyte as depicted is a target protein that is being produced by cells in the sample. A fluorescent label is associated with or bound to an antibody that is specific for and/or binds the target protein. Panel (A) is a schematic diagram of the various biological components present in one or more pores before any force is applied to the array. The particles are associated with the fluorescent label due to antigen binding to the target protein, which is also bound to the labelled antibody. Panel (A) represents a time point shortly after addition of sample to the pore, because some target protein remains unbound to the antigen and/or antibody. In some embodiments, the array would then be incubated and/or stirred to facilitate target protein binding. After optional incubation, panel (B) depicts the pore following the accumulation of the particles to the detection surface by application of a magnetic force. In this embodiment, the detection surface is the open surface of the liquid in the pore. In this example, the electromagnetic (EM) signal from the label bound to the magnetic particle is detected from the pore surface.

In additional embodiments, a method is provided for detecting two or more analytes in a sample. The method includes adding to the reaction vessel a second label that emits electromagnetic radiation and second particles that are different from the first particles based upon at least one of the following properties: shape, size, density, magnetic permittivity, charge, and optical coating. As described above, the second label is bound to the second particles or the second label becomes bound to the second particles as a result of the presence or absence of a second analyte in the sample (e.g., an enzyme is bound to the particles or a label becomes bound as a result of a competitive or sandwich assay). The second particles are accumulated at a second detection surface to inhibit the transmission of electromagnetic radiation into and out of the sample through the second detection surface. The presence or amount of electromagnetic radiation emitted from the second particles can be detected at the second detection surface.

In various embodiments first particles for detecting a first analyte accumulate at the first detection surface as a result of a first force and the second particles accumulate at the second detection surface as a result of second force, wherein the first force and the second force are independently selected from the group consisting of gravitational, magnetic, electrical, centrifugal and acoustic force as described above. The first force and the second force are applied to the sample, and detection can be accomplished either simultaneously or sequentially.

Particles

High sensitivity is achieved by concentrating particles at the detection surface when the particles have the ability to shutter the sample, for example inhibit excitation energy from an in-solution fluorochrome and the transmission of background signal to a detector. Suitable particles are readily commercially available and a wide variety of particles can be used according to the methods disclosed herein as long as the particles can accumulate and inhibit electromagnetic radiation through the detection surface. In various embodiments, the particles are partially or fully opaque. In certain embodiments, the particles absorb electromagnetic radiation, for example the particles have an efficiency of absorbance of at least about 10 percent, for example, 25, 30, 35, 40, 45, 50, 55, 60, 65, 70, 75, 80, 85, 90, 95 or 100 percent.

In various embodiments, the size of the particles ranges from nanoscale to about one-third the size of the cross section of a reaction vessel. For example, when a microcavity is about 20 microns in diameter, the particle can be about 0.01 to 7 microns in diameter. The size of the particles should allow for accumulation and of particles at the detection surface of the vessel so that the accumulation of the particles inhibit electromagnetic radiation from entering or exiting the sample solution. For example, when the reaction vessel is a micropore, the sample solution will form a meniscus with the wall of the micropore. When the micropore is open at both ends, a meniscus forms at both the top and the bottom of the micropore. The particles should be able to accumulate at the meniscus at the top or bottom of the micropore such that electromagnetic radiation is prevented for existing or entering the sample solution in the micropore.

In specific embodiments, the particle diameter ranges from about 0.01 microns to about 50 microns, depending on the size of the vessel used. In various embodiments, the particles range in size from about 0.1 to 15 microns, about 0.5 to 10 microns, and about 1 to about 5 microns.

In certain embodiments, the particles comprise a metal or carbon. Non-limiting examples of suitable metals include gold, silver, and copper. Other metallic materials are suitable for use in binding assays as is well known to those of skill in the art.

In one embodiment, the particles are magnetic such that magnetic force can be used to accumulate the particles at the detection surface of each reaction vessel, e.g., the meniscus of a micro-cavity.

The surface chemistry of the particles may be functionalized to provide for binding to sample components as is well known to those of skill in the art. For example, the particles are coupled with streptavidin, biotin, oligo(dT), protein A &G, tagged proteins, and/or any other linker polypeptides. The very high binding affinity of the streptavidin-biotin interaction is utilized in a vast number of applications. Streptavidin bound particles will bind biotinylated nucleic acids, antibodies or other biotinylated ligands and targets. Biotinylated antigens are a useful example of the products that could be bound to the particles for screening for analytes. In a specific embodiment, the particles are DYANABEAD® particles (Invitrogen, Carlsbad, CA) coupled to several different ligands. For example, oligo(dT), protein A &G, tagged proteins (His, FLAG), secondary antibodies, and/or streptavidin. (Part No. 112-05D, Invitrogen, Carlsbad, CA).

In some embodiments, particles having different magnetic permittivities can be used to provide independent control of the magnetic forces acting on the particles. In other embodiments, other properties of the particles can be used to expand the multiplexing capability of the assays done in each cavity. When added to a sample, particles bind to the desired target (cells, pathogenic microorganisms, nucleic acids, peptide, protein or protein complex etc). This interaction relies on the specific affinity of the ligand on the surface of the particles. Alternatively, the particles conjugated to substrate for an enzyme can be added to the sample, where the enzyme/analyte in the sample either quenches the ability of the substrate to fluoresce or activates the substrate to be fluorescent (e.g., enzyme mediated cleavage of the substrate).

Another embodiment uses magnetic particles having different shapes, densities, sizes, charges, magnetic permittivity, or optical coatings. This allows different probes (i.e., binding partners) to be put on the different particles and the particles could be probed separately by adjusting how and when the magnetic field or other force is applied. Sedimentation rates can also be used to separate the particles by size, shape and density and expand the multiplexing capability of the assays done in each cavity.

For example, one particle could contain the target antigen which would allow determination of the affinity of the antibodies produced in each cavity to the target. The other particle located in each cavity could contain a wide range of antigens on the same particle which allow measurement of the specificity of the antibody. The settling times of particles having different sizes or densities when no magnetic field can be exploited. The particles with the faster settling times can be detected by scanning a detection surface at the bottom of the cavity. If the particles with the slower settling time had a higher magnetic permittivity, they could be attracted to the bottom of the cavity before the other particles only when the magnetic field was applied.

Similarly, some of the particles can be magnetic and the others not, and the magnetic particles can be drawn to the top of the cavities by an applied magnetic field and there detected, while the nonmagnetic particles settle to the bottom of the cavity and can be detected there. Using these types of methods, both sensitivity and specificity of the antibodies can be measured in the same well.

In certain embodiments, the particles are used to mix the content of the receptacles. For example, magnetic particles are subjected to and alternating or intermittent magnetic field(s) during an incubation step. The movement and settling of the particles results in the mixing of the contents of the reaction vessel.

Any suitable binding partner with the requisite specificity for the form of molecule, e.g., a marker, to be detected can be used. If the molecule, e.g., a marker, has several different forms, various specificities of binding partners are possible. Suitable binding partners are known in the art and include antibodies, aptamers, lectins, and receptors. A useful and versatile type of binding partner is an antibody.

The method for detecting an analyte in a sample disclosed herein allows for the simultaneous testing of two or more different antigens per pore. Therefore, in some embodiments, simultaneous positive and negative screening can occur in the same pore. This screening design improves the selectivity of the initial hits. In certain embodiments, the second antigen tested can be a control antigen. Use of a control antigen is useful for normalizing biological element concentration across the various pores in the array. A non-limiting example would be using a first antigen specific for an analyte of interest, and a second antigen that is non-specific for all proteins, such as the –N or –C terminal. Therefore the results of pores of interest can be quantified by comparing the signal to total protein concentration.

In some embodiments, the second antigen is associated with second particles that are different from the first particles. The particles can vary by least one of the following properties: shape, size, density, magnetic permittivity, charge, and optical coating. The second label can therefore associate with the second particles as a result of the presence or absence of a second analyte in the sample, and processed using motive forces as described below.

In another embodiment, the particles non-specifically bind sample components. For example, particles can be functionalized to non-specifically bind all protein in a sample, which allows for normalization of protein content between sample in an array.

Antibodies

The term "antibody," as used herein, is a broad term and is used in its ordinary sense, including, without limitation, to refer to naturally occurring antibodies as well as non-naturally occurring antibodies, including, for example, single chain antibodies, chimeric, bifunctional and humanized antibodies, as well as antigen-binding fragments thereof. It will be appreciated that the choice of epitope or region of the molecule to which the antibody is raised will determine its specificity, e.g., for various forms of the molecule, if present, or for total (e.g., all, or substantially all, of the molecule).

Methods for producing antibodies are well-established. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments that mimic antibodies can be prepared from genetic information by various procedures (Antibody Engineering: A Practical Approach (Borrebaeck, C., ed.), 1995, Oxford University Press, Oxford; J. Immunol. 149, 3914-3920 (1992)). Monoclonal and polyclonal antibodies to molecules, e.g., proteins, and markers also commercially available (R and D Systems, Minneapolis, Minn.; HyTest Ltd., Turk, Finland; Abcam Inc., Cambridge, Mass., USA; Life Diagnostics, Inc., West Chester, Pa., USA; Fitzgerald Industries International, Inc., Concord, Mass., USA; BiosPacific, Emeryville, Calif.).

In some embodiments, the antibody is a polyclonal antibody. In other embodiments, the antibody is a monoclonal antibody.

Capture binding partners and detection binding partner pairs, e.g., capture and detection antibody pairs, can be used in embodiments of the invention. Thus, in some embodiments, a heterogeneous assay protocol is used in which, typically, two binding partners, e.g., two antibodies, are used. One binding partner is a capture partner, usually immobilized on a particle, and the other binding partner is a detection binding partner, typically with a detectable label attached. Such antibody pairs are available from several commercial sources, such as BiosPacific, Emeryville, Calif. Antibody pairs can also be designed and prepared by methods well-known in the art.

In a particular embodiment, the antibody is biotinylated or biotin labelled. In another embodiment, the antibody is anti-GFP.

In one embodiment, there is a second imaging component that binds all members of the analyte of interest non-specifically. Therefore this signal can be read to normalize the quantity of fluorescence from pore to pore. One example is an antibody that will bind all proteins at the N or C terminal. For the control component, the microparticles that are bound to the target element can be accumulated at one detection surface, while the microparticles that are bound to the control element accumulate at another detection surface. Alternatively, the microparticles that bind the target and the control can be detected at the same detection surface by exploiting a difference in the particles that allows them to be at the surface at different times. Accordingly, detection of the labels at the detection window can occur sequentially.

Labels

Several strategies that can be used for labeling binding partners to enable their detection or discrimination in a mixture of particles are well known in the art. The labels may be attached by any known means, including methods that utilize non-specific or specific interactions. In addition, labeling can be accomplished directly or through binding partners.

Emission, e.g., fluorescence, from the moiety should be sufficient to allow detection using the detectors as described herein. Generally, the compositions and methods of the invention utilize highly fluorescent moieties, e.g., a moiety capable of emitting electromagnetic radiation when stimulated by an electromagnetic radiation source at the excitation wavelength of the moiety. Several moieties are suitable for the compositions and methods of the invention.

Labels activatable by energy other than electromagnetic radiation are also useful in the invention. Such labels can be activated by, for example, electricity, heat or chemical reaction (e.g., chemiluminescent labels). Also, a number of enzymatically activated labels are well known to those in the art.

Typically, the fluorescence of the moiety involves a combination of quantum efficiency and lack of photobleaching sufficient that the moiety is detectable above background levels in the disclosed detectors, with the consistency necessary for the desired limit of detection, accuracy, and precision of the assay.

Furthermore, the moiety has properties that are consistent with its use in the assay of choice. In some embodiments, the assay is an immunoassay, where the fluorescent moiety is attached to an antibody; the moiety must have properties such that it does not aggregate with other antibodies or proteins, or experiences no more aggregation than is consistent with the required accuracy and precision of the assay.

In some embodiments, fluorescent moieties dye molecules that have a combination of 1) high absorption coefficient; 2) high quantum yield; 3) high photostability (low photobleaching); and 4) compatibility with labeling the molecule of interest (e.g., protein) so that it may be analyzed using the analyzers and systems of the invention (e.g., does not cause precipitation of the protein of interest, or precipitation of a protein to which the moiety has been attached).

A fluorescent moiety may comprise a single entity (a Quantum Dot or fluorescent molecule) or a plurality of entities (e.g., a plurality of fluorescent molecules). It will be appreciated that when "moiety," as that term is used herein, refers to a group of fluorescent entities, e.g., a plurality of fluorescent dye molecules, each individual entity may be attached to the binding partner separately or the entities may be attached together, as long as the entities as a group provide sufficient fluorescence to be detected.

In some embodiments, the fluorescent dye molecules comprise at least one substituted indolium ring system in which the substituent on the 3-carbon of the indolium ring contains a chemically reactive group or a conjugated substance. Examples include Alexa Fluor molecules.

In some embodiments, the labels comprise a first type and a second type of label, such as two different ALEXA FLUOR® dyes (Invitrogen), where the first type and second type of dye molecules have different emission spectra.

A non-inclusive list of useful fluorescent entities for use in the fluorescent moieties includes: ALEXA FLUOR® 488, ALEXA FLUOR® 532, ALEXA FLUOR® 647, ALEXA FLUOR® 700, ALEXA FLUOR® 750, Fluorescein, B-phycoerythrin, allophycocyanin, PBXL-3, Atto 590 and Qdot 605.

Labels may be attached to the particles by any method known in the art, including, absorption, covalent binding, biotin/streptavidin or other binding pairs. In addition, the label may be attached through a linker. In some embodiments, the label is cleaved by the analyte, thereby releasing the label from the particle. Alternatively, the analyte may prevent cleavage of the linker.

Arrays

In one embodiment, the reaction vessels for use with the invention are included in an extreme density porous array. For instance, micro-pore arrays contemplated herein can be manufactured by bundling millions or billions of silica capillaries and fusing them together through a thermal process. Such a fusing process may comprise the steps including but not limited to; i) heating a capillary single draw glass that is drawn under tension into a single clad fiber; ii) creating a capillary multi draw single capillary from the single draw glass by bundling, heating, and drawing; iii) creating a capillary multi-multi draw multi capillary from the multi draw single capillary by additional bundling, heating, and drawing; iv) creating a block assembly of drawn glass from the multi-multi draw multi capillary by stacking in a pressing block; v) creating a block pressing block from the block assembly by treating with heat and pressure; and vi) creating a block forming block by cutting the block pressing block at a precise length (e.g., 1 mm).

In one embodiment, the method further comprises slicing the silica capillaries, thereby forming a very high-density glass micro-pore array plate. It will be appreciated that the array of micro-pores for use in the present invention can be formed by any suitable method. In one embodiment, the capillaries are cut to approximately 1 millimeter in height, thereby forming a plurality of micro-pores having an internal diameter between approximately 1.0 micrometers and 500 micrometers. In one embodiment, the micro-pores range between approximately 10 micrometers and 1 millimeter long. In one embodiment, the micro-pores range between approximately 10 micrometers and 1 centimeter long. In one embodiment, the micro-pores range between approximately 10 micrometers and 10 millimeter long. In one embodiment, the micro-pores range between approximately 10 micrometers and 100 millimeter long. In one embodiment, the micro-pores range between approximately 0.5 millimeter and 1 meter long.

Figure 2:
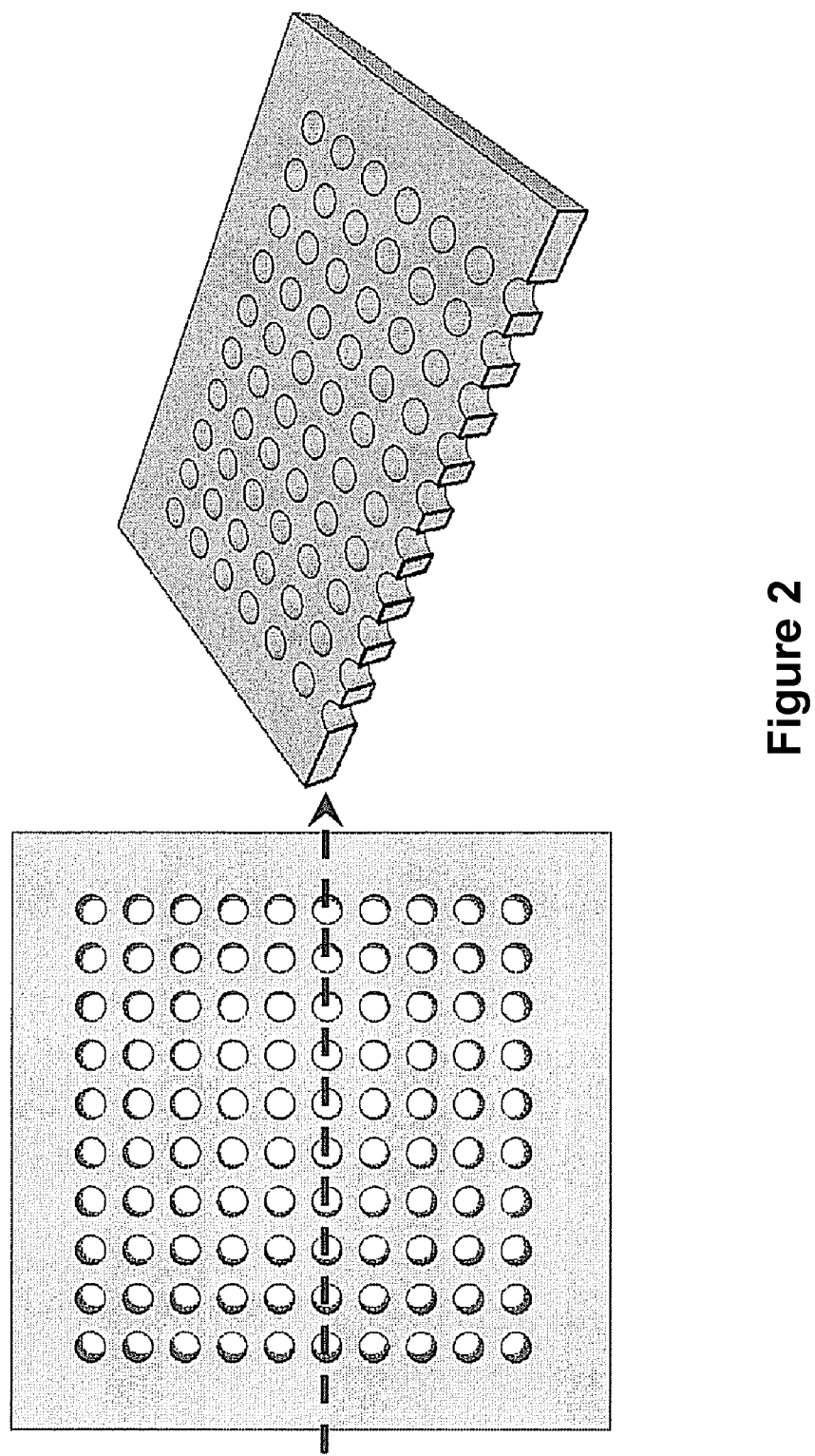
FIG. 2 illustrates an example of one embodiment of a high density array as used according to the disclosure.

Such processes form a very high-density micro-pore array that may be used in the present invention. In an exemplary array, each micro-pore has a 5 μm diameter and approximately 66% open space (i.e., representing the lumen of each micropore). In some arrays, the proportion of the array that is open ranges between about 50% and about 90%, for example about 60 to 75%, such as a micro-pore array provided by Hamamatsu that having an open area of about 67%. In one particular example, a 10×10 cm array having 5 μm diameter micropores and approximately 66% open space has about 330 million micro-pores. See, e.g., FIG. 2.

In various embodiments, the internal diameter of micro-pores ranges between approximately 1.0 micrometers and 500 micrometers. In some arrays, each of said micro-pores can have an internal diameter in the range between approximately 1.0 micrometers and 300 micrometers; optionally between approximately 1.0 micrometers and 100 micrometers; further optionally between approximately 1.0 micrometers and 75 micrometers; still further optionally between approximately 1.0 micrometers and 50 micrometers, still further optionally, between approximately 5.0 micrometers and 50 micrometers.

In some arrays, the open area of the array comprises up to 90% of the open area (OA), so that, when the pore size varies between 10 μm and 500 μm, the number of micro-pores per cm of the array varies between 458 and 1,146,500, as is represented in the table below. In some arrays, the open area of the array comprises about 67% of the open area, so that, when the pore size varies between 10 μm and 500 μm, the number of micro-pores per square cm of the array varies between 341 and 853,503, as is represented in the table below. It will be appreciated that, with a pore size of 1 μm and up to 90% open area, each square cm of the array will accommodate up to approximately 11,466,000 micro-pores.

| Pore diameter (um) | No of pore (90% OA) | No of pores (67% OA) |
| --- | --- | --- |
| 500 | 458 | 341 |
| 300 | 1275 | 948 |
| 100 | 1150 | 8535 |
| 75 | 20,380 | 15,172 |
| 50 | 45.860 | 34,140 |
| 10 | 1,146,500 | 853,503 |
| 1 | 11,465,967 | 8,535,031 |

In one particular embodiment, a micropore array can be manufactured by bonding billions of silica capillaries and then fusing them together through a thermal process. After that slices (0.5 mm or more) are cut out to form a very high aspect ratio glass micro perforated array plate. See, International Application PCT/EP2011/062015 (WO2012/007537), filed 13 Jul. 2011 date, which is incorporated by reference herein in its entirety. Arrays are also commercially available, such as from Hamamatsu Photonics K. K., (Part No. J5022-19) and other manufacturers. In some embodiments, the micropores of the array are closed at one end with a solid substrate attached to the array.

Thus, in addition to being faster and easier to use, the ability to detect produced proteins allows this micro-pore array to provide higher resolution than current methods that rely upon the target molecule being expressed on the surface of a display vector (i.e. phage display, ribosome display, mammalian cell display, bacterial cell display or yeast display). Additional benefits of this array as compared to phage display methods include the ability to simultaneously test two (or more) target molecules per pore (i.e. positive and negative screening) and not being limited by the size of the protein being examined since phage-displayed proteins have to be small.

In another embodiment, the present invention contemplates a method for loading array comprising contacting a solution comprising a plurality of cells with the array to form a loaded array. In one embodiment, loading a mixture of antibody secreting cells, e.g., E. coli, evenly into all the micro-pores comprises placing a 500 μL droplet on the upper side of the array and spreading it over all the micro-pores. The heterogeneous population of cells can be loaded onto the micro-pore array. In one embodiment, an initial concentration of approximately $10^9$ cells in the 500 μL, droplet results in approximately 3 cells (or sub-population) per micro-pore. In one embodiment, each micro-pore has an approximate volume of between 20-80 pL (depending on the thickness of the glass capillary plate of between 250 μm to 1 mm). Once the micro-pores are loaded and incubated overnight, each micro-pore should then contain approximately 2,000-3,000 cells per micro-pore. In one embodiment, the cells may be cultivated for up to forty-eight hours without loss of viability in order to maximize the proliferation yield. Although it is not necessary to understand the mechanism of an invention, it is believed that "spreading" the droplet over all the micro-pores provides for optimal distribution of cells in the various micro-pores. Theoretically, adding a drop to the micro-pore array should fill all pores evenly. However, an empirical evaluation demonstrated that surface tension actually prevents the drop from entering the central micro-pores. If the drop is spread evenly over the micro-pore array surface the surface tension is removed. Consequently, if the drop is placed straight down on the micro-pore array, only the pores at the edge of the drop fill due to reduced surface tension (also evaporation recedes the drop so that the liquid is no longer held in suspension). This causes a halo ring effect following detection of the appropriate analyte. See, WO2012/007537.

In one embodiment, the solution comprises approximately three (3) microliters. In one embodiment, the plurality of cells may be selected from the group comprising animal cells, plant cells, and/or microbial cells. In one embodiment, the plurality of cells comprise E. coli cells. In one embodiment, the E. coli cells secrete at least one recombinant compound of interest. In one embodiment, the recombinant compound of interest has an affinity for the binding partner.

Although it is not necessary to understand the mechanism of an invention, it is believed that, if there are approximately $10^9$ cells in an approximate 500 μL-solution then, on average, there should be approximately three (3) cells per micro-pore for an array having approximately $3-4\times10^6$ micro-pores. It should be noted that the exact number will depend on the number of pores in the array. For example, if an array has approximately $3-4\times10^6$ micro-pores, it therefore, would have approximately 500-100 cells/pore. In one embodiment, each micro-pore comprises a volume of ranging between approximately 20-80 pico liters.

In certain embodiment, the sidewalls of the cavities of the arrays are not transmissive to electromagnetic radiation, or the cavities are coated with a material that prevents the transmission of electromagnetic radiation between cavities of the arrays. Suitable coating should not interfere with the binding reaction within the cavities or the application of forces to the cavities. Exemplary coatings include sputtered nanometre layers of gold, silver and platinum.

In some embodiments, the cavities of the array have a hydrophilic surface which can spontaneously uptake the solution into the pore.

Sample Dilution, Preparation, Incubation

The sample containing the population and/or library of biological samples may require preparation steps prior to distribution to the array. In some embodiments, these preparation steps include an incubation time. The incubation time will depend on the design of the screen. Example times include 5 minutes, 1 hour, and/or 3 hours. Example ranges are 1 second to 72 hours.

In certain embodiments, the heterogeneous population of biological elements is expanded in media prior to adding and/or loading onto the array. For certain applications, the media and element mixture is loaded into the array while in the exponential growth phase.

In other embodiments, the sample containing the heterogeneous population and/or library of biological samples may require preparation steps after addition to the array. In other embodiments, each element within each pore is expanded (cells grown, phages multiplied, proteins expressed and released, etc.) during an incubation period. This incubation period allows the biological elements to produce bioreactive molecules.

For some embodiments, each pore has a volume of media that will allow certain biological elements to replicate. In specific embodiments, the volume of media is about 20 picoliter, which provides sufficient media to allow most single cells within a pore to replicate multiple times. The array can optionally be incubated at any temperature, humidity, and time for the biological elements to expand and produce the target proteins. Incubation conditions can be determined based on experimental design as is routine in the art.

Concentration, Conditions, Loading

In a specific embodiment, the array is designed such that some or all pores contain a single biological element to screen for the analyte. The concentration of the heterogeneous mixture of biological elements is therefore calculated according to the design of the array and desired analytes to identify. In embodiments where protein-producing cells are being screened, the method is advantageous because it eliminates the clonal competition and thus can screen a much larger diversity.

In one embodiment, the method of the present invention contemplates the concentration of the suspension of heterogeneous population of cells and the dimensions of the array are arranged such that 1-1000 biological elements, optionally, 1-500 biological elements, further optionally, 1-100 biological elements, still further optionally 1-10 biological elements, still further optionally, 1-5 biological elements, are distributed into at least one of said micropores of the array.

The volume of the drop will depend on several variables, including for example the desired application, the concentration of the heterogeneous mixture, and/or the desired dilution of biological elements. In one specific embodiment, the desired volume on the array surface is about 1 microliter per square millimeter. The concentration conditions are determined such that the biological elements are distributed in any desired pattern or dilution. In a specific embodiment, the concentration conditions are set such that in most pores of the array only single elements are present. This allows for the most precise screening of single elements.

These concentration conditions can be readily calculated. By way of example, in a cell screen, if the ratio of protein-producing cells to pores is about 1 to 3, an array with $10^9$ pores could be loaded with $3 \times 10^8$ different protein-producing cells in a 6 mL volume (6 mL=20 picoliter/pore$\times 3 \times 10^8$ pores), the vast majority of the pores will contain at most a single clone. In certain other embodiments, single biological elements are not desired in each pore. For these embodiments, the concentration of the heterogeneous population is set so that more than one biological element is found in each pore. For example, FIG. 3 shows the addition of a mixture of protein-producing cells (bacterial cells: E. coli) being loaded into the pores of an array by placing a 1.0 mL drop on one side of the array and spreading it over all of the pores.

The screening may also be used to enrich a population of biological elements, such as biological cells. For instance, if the number of biological elements in a population exceeds the number of pores in the array, the population can be screened with more than one element in each pore. The contents of the pores that provide a positive signal can then be extracted to provide a subpopulation. The subpopulation can be screened immediately or, when the subpopulation is cells, it can be expanded. The screening process can be repeated until each pore of the array contains only a single element. The screen can also be applied to detect and/or extract the pore that indicates the desired analyte is present therein. Following the selection of the pore, other conventional techniques may be used to isolate the individual analyte of interest, such as techniques that provide for higher levels of protein production.

After the biological elements have been loaded into the array, additional molecules or particles can be added or removed from the array without disturbing the biological elements. For example, any molecules or particles useful in the detection of the biological elements can be added. These additional molecules or particles can be added to the array by introducing liquid reagents comprising the molecules or particles to the top of the array, such as for example by adding drop-wise as described in relation to the addition of the biological elements. To remove specific molecules from an array comprising biological elements, a solution can be prepared that is free from the selected molecule to be removed but contains all the rest of the molecules that are present in the pore array at the desired concentration. The droplet is added to the array as previously described. After the contents of the pore array equilibrate with the droplet of this solution, the concentration of the selected molecule in the array will be reduced. The reduction amount depends on the volume of the added drop and the total volume contained in the array. To further reduce the concentration of the selected molecule, this step may be repeated after removing the first drop from the top of the array and then adding a second drop of liquid. Liquid can be removed from the top of the array by, for example, blotting the array with a paper towel or with a pipette.

In certain embodiments, the top of the array is sealed with a membrane following the addition of sample to the pores in order to reduce evaporation of the media from the pores. One or more substantially gas and/or liquid impermeable membranes can be used to seal the surfaces of the array following the addition of a sample to the pores. For example, typical food-service type plastic wraps such as polyvinylidene fluoride (PVDF) are suitable. In another embodiment, the membrane allows water vapor to equilibrate with the top liquid layer of the liquid in the pore, which can help prevent evaporation. For example, a film placed in contact with the top surface of the micropore array, with water place on top of the film, would trap the contents of the pores within each individual pore, but would allow water or media to flow into the pores. Examples of useful members are nitrocellulose and NAFION® membranes. A similar arrangement could be obtained with a porous form of a polytetrafluoroethylene membrane (e.g., GORE-TEX® fabrics) having very small holes (e.g., 10-100 nm) that would trap any cells in the pores but allow water, media and other reagents to pass into the pores.

Extraction of Microcavity Content

Based on the optical information received from a detector associated with the array of cavities, target cavities with the desired properties are identified and their contents extracted for further characterizations and expansion. The disclosed methods are advantageous because they maintain the integrity of the biological elements in the cavities. Therefore the methods disclosed herein provide for the display and independent recovery of a target population of biological elements from a population of up to billions of target biological elements. This is particularly advantageous for embodiments where cells are screened.

Figure 4:
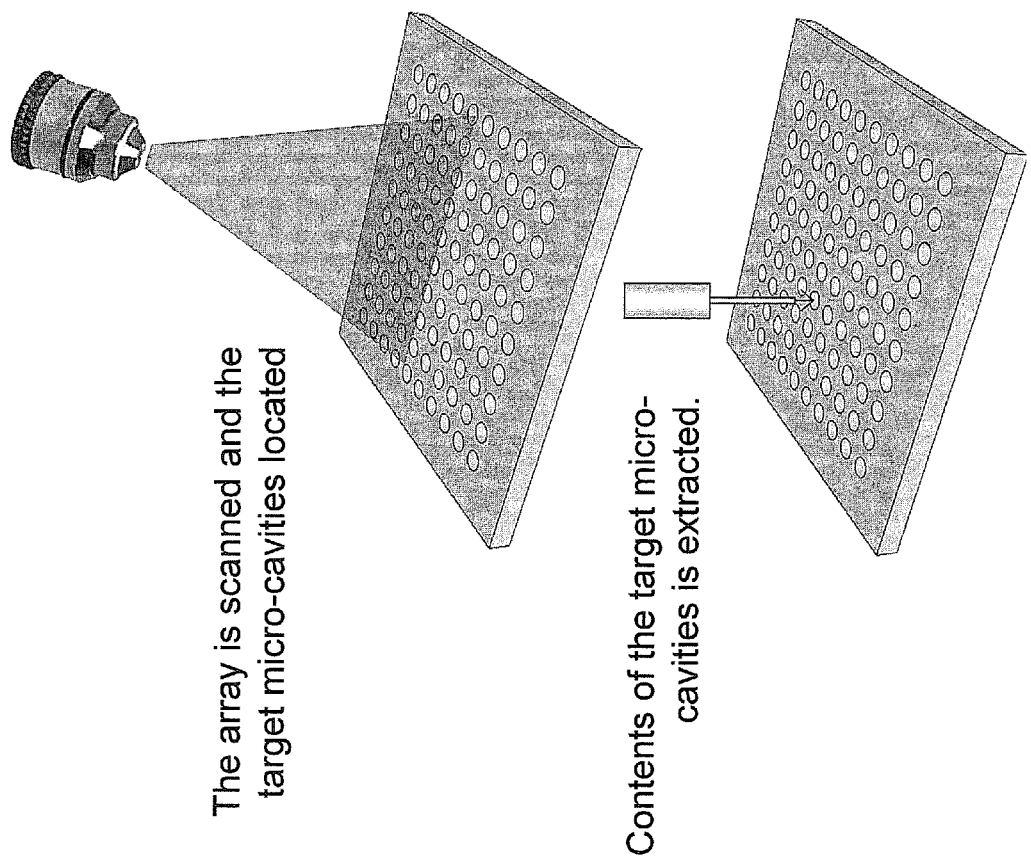
FIG. 4 illustrates one embodiment of a method for scanning and identifying the pores that produce signal. These pores will appear as high intensity spots, due to the accumulation of labelled particles at the detection surface of the pore. In one assay design as embodied herein, such as a sandwich assay, pores that have strong signal will be selected for extraction and further preparation. In another assay design as embodied herein, such as an enzyme activity assay, the pores that have strong signal will not be selected. Instead the pores that show the least amount of signal, or no signal, will be selected.
Figure 6:
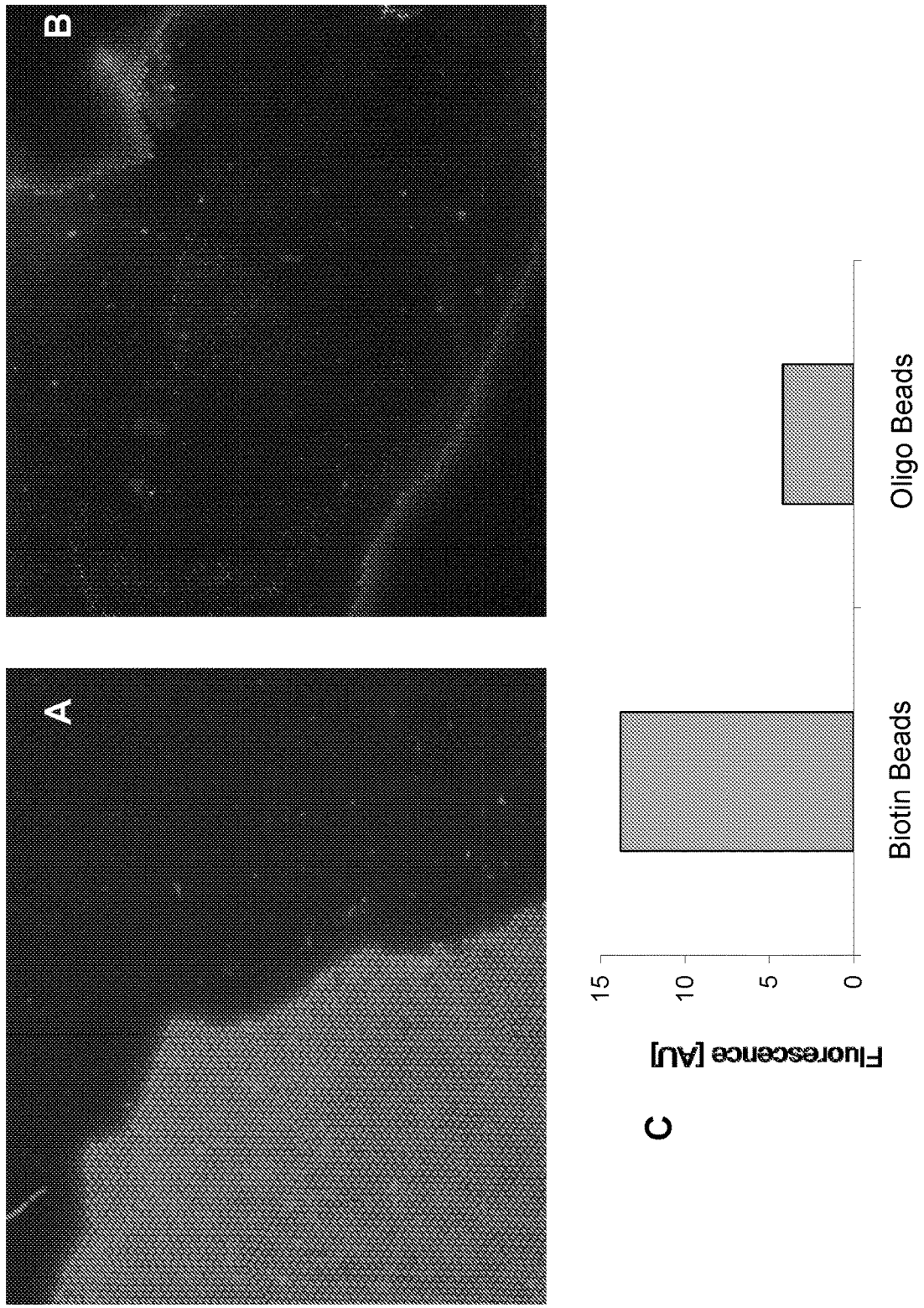
FIG. 6 illustrates that a protein binding and detection assay can be performed directly in the pores as disclosed herein. In this embodiment, all of the pores of the array comprise fluorescently labelled (Atto 590) streptavidin and magnetic beads coated with biotin (Part A: Positive control) and Oligo(dT)$_{25}$ (Part B: Neg. Control).

For example, after pulling the particles to the top or bottom of the pores, the signals from each pore are scanned to locate the binding events of interest (See FIG. 4). This identifies the pores of interest. Individual pores containing the desired clones can be extracted using a variety of methods. For all extraction techniques, the extracted cells or material can be expanded through culture or amplification reactions and identified for the recovery of the protein, nucleic acid or other biological element. As described above, multiple rounds of screening are also contemplated. Following each screening, one or more cavities of interest can be extracted as described herein. The contents of each cavity can then be screened again until the desired specificity is achieved. In certain embodiments, the desired specificity will be a single biological element per pore. In these embodiments, extraction may follow each round of the screening before the cavities include only a single element.

In one embodiment, the method includes isolating cells located in the micropores by pressure ejection. For example, a separated micro-pore array is covered with a plastic film. In one embodiment, the method further provides a laser capable of making a hole through the plastic film, thereby exposing the spatially addressed micro-pore. Subsequently, exposure to a pressure source (e.g., air pressure) expels the contents from the spatially addressed micro-pore. See WO2012/007537.

Another embodiment is directed to a method of extracting a solution including a biological element from a single microcavity in a microcavity array. In this embodiment, the microcavity is associated with an electromagnetic radiation absorbent material so that the material is within the cavity or is coating or covering the microcavity. Extraction occurs by focusing electromagnetic radiation at the microcavity to generate an expansion of the sample or of the material or both or evaporation that expels at least part of the sample from the microcavity. The electromagnetic radiation source may be the same or different than the source that excites a fluorescent label (See FIG. 1, which depicts the same electromagnetic radiation source for both excitation of the label and extraction of components of a cavity of the array). The source may be capable of emitting multiple wavelengths of electromagnetic radiation in order to accommodate different absorption spectra of the materials and the labels.

Figure 9:
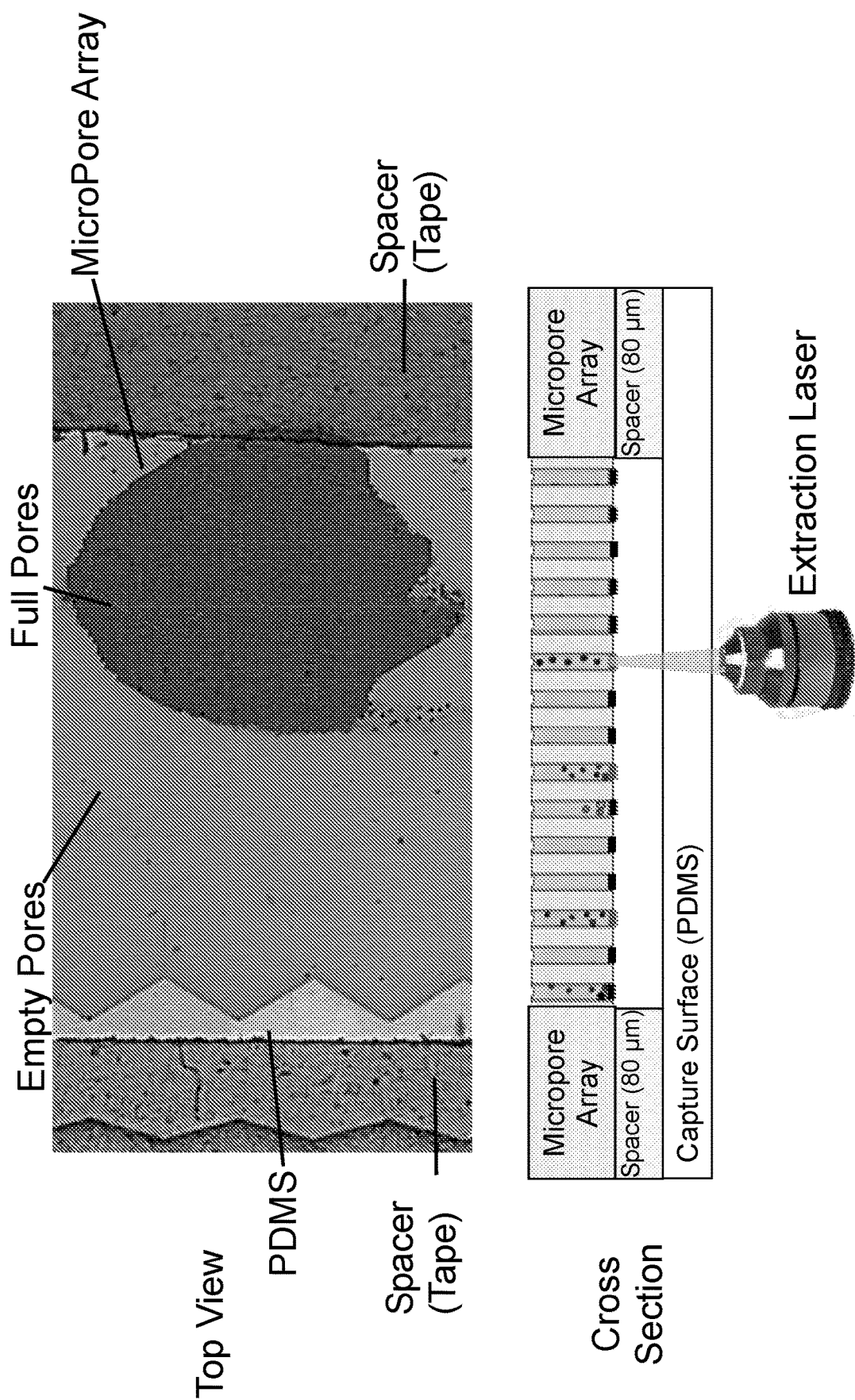
FIG. 9 is a schematic diagram of one method of single pore extraction.

Subjecting a selected microcavity to focused electromagnetic radiation can cause an expansion of the electromagnetic radiation absorbent material, which expels sample contents onto a substrate for collecting the expelled contents. For example, FIG. 9 shows the extraction of a particular microcavity of interest. Cavities of interest are selected and then extracted by focusing a 349 nm solid state UV laser at 20-30% intensity power. In one example, the source is a frequency tripled, pulsed solid-state Nd:YAG or Nd:YVO4 laser source emitting about 1 microJoule to about 1 milliJoule pulses in about a 50 nanosecond pulse. Both continuous wave lasers with a shutter and pulsed laser sources can be used. The laser should have sufficient beam quality so that it can be focused to a spot size with a diameter roughly the same or smaller than the diameter of the pore. Power levels will depend on the size of the cavity and its contents.

As understood by one of skill in the art, the electromagnetic radiation emission spectra from the electromagnetic radiation source must be such that there is at least a partial overlap in the absorption spectra of the electromagnetic radiation absorbent material associated with the cavity. The extracted contents can then be located on the capture surface (See FIG. 9). When the extracted contents include cells, they can be expanded to obtain the protein, antibody or other element of interest.

In some embodiments, the capture surface comprises a hygroscopic layer upon which the contents of the cavity are expelled. The hygroscopic layer attracts water and prevents the deformation of the optical surface allowing clear imaging of the cavity contents. In certain embodiments, the layer is a hygroscopic composition, such as solution comprising glycerol. The layer can be applied, for example, by spreading, wiping or spraying and should create a uniform dispersion on the surface. Typically, the layer is about 10-100 μm thick, as long as the layer does not distort the EM radiation passing through the layer and does not touch the array above.

Materials within the cavity can be, for example, the particles used in the binding assays as described above. Accordingly, the particles may have a property that allows the particles to respond to a force in order to accumulate at a detection surface, and also include an electromagnetic radiation absorbent material, e.g., DYNABEAD® particles. In various embodiments, energy is applied to the particles while they are accumulated at the detection surface after the signal at the detection surface is detected (by continued or reapplication of a force), or the force is removed so that the particles return to the sample solution. Alternatively, the cavities include particles or other materials that do not participate in the binding reactions but are present to provide extraction of the contents as described herein. These particles may be functionalized so that they bind to the walls of the micro-cavities independent of the binding reaction of the assay. Similar materials can be used to coat or cover the micropores, and in particular, high expansion materials, such as EXPANCEL® coatings (AkzoNobel, Sweden). In another embodiment the EXPANCEL® material can be supplied in the form of an adhesive layer that is bonded to one side of the array so that each pore is bonded to an expansion layer.

Focusing electromagnetic radiation at a microcavity can cause the electromagnetic radiation absorbing material to expand, which causes at least part of the liquid volume of the cavity to be expelled. Heating the material may also cause a rapid expansion of the contents of the cavity. In some embodiments, a portion of the of the contents (up to 50%)

are expanded up to 1600 times by heating, which causes a portion of the remainder of the contents to be expelled from the cavity.

Without rapid expansion of the material or cavity contents, heating can cause evaporation of the contents, which can be collected by condensing the contents on a substrate. For example, the substrate can be a hydrophobic micropillar placed at or near the opening of the cavity. Expulsion of the contents may also occur as the sample evaporates and condenses on the walls of a capillary outside the meniscus, which causes the meniscus to break and release the contents of the capillary.

Micro-cavities, such as a micropore, can be open at both ends, with the contents being held in place by hydrostatic force. During the extraction process, one of the ends of the cavities can be covered to prevent expulsion of the contents from the wrong end of the cavity. The cavities can be covered in the same way as, for example, the plastic film described above. Also, the expansion material may be bonded as a layer to one side of the array.

Apparatus

Detection of analytes in accordance with the invention requires, in some embodiments, the use of an apparatus capable of applying electromagnetic radiation to the sample, and in particular, to an array of vessels, such as a microarray. The apparatus must also be capable of detecting electromagnetic radiation emitted from the sample, and in particular from the detection surface of the sample vessel.

Any type of electromagnetic radiation source may be used according to the disclosure without departing from the scope of the invention. In one embodiment, the electromagnetic radiation source of the apparatus is broad spectrum light or a monochromatic light source having a wavelength that matches the wavelength of at least one label in a sample. In a further embodiment, the electromagnetic radiation source is a laser, such as a continuous wave laser. In yet a further embodiment, the electromagnetic source is a solid state UV laser. A non-limiting list of other suitable electromagnetic radiation sources include: argon lasers, krypton, helium-neon, helium-cadmium types, and diode lasers. In some embodiments, the electromagnetic source is one or more continuous wave lasers, arc lamps, or LEDs.

In some embodiments, the apparatus comprises multiple electromagnetic sources. In other embodiments, the multiple electromagnetic (EM) radiation sources emit electromagnetic radiation at the same wavelengths. In other embodiments, the multiple electromagnetic sources emit different wavelengths in order to accommodate the different absorption spectra of the various labels that may be present in the sample.

In some embodiments, the electromagnetic radiation source is located such that an array of micropores can be contacted with electromagnetic radiation. In some embodiments, the electromagnetic radiation source is located such that the detection surface of a vessel can be subjected to electromagnetic radiation.

The apparatus also includes a detector that receives electromagnetic (EM) radiation from the label(s) in the sample, array. The detectors can identify at least one vessel (e.g., a micropore) emitting electromagnetic radiation from one or more labels.

In one embodiment, light (e.g., light in the ultra-violet, visible or infrared range) emitted by a fluorescent label after exposure to electromagnetic radiation is detected. The detector or detectors are capable of capturing the amplitude and duration of photon bursts from a fluorescent moiety, and further converting the amplitude and duration of the photon burst to electrical signals.

Once a particle is labeled to render it detectable, or if the particle possesses an intrinsic characteristic rendering it detectable, any suitable detection mechanism known in the art may be used without departing from the scope of the present invention, for example a CCD camera, a video input module camera, a Streak camera, a bolometer, a photodiode, a photodiode array, avalanche photodiodes, and photomultipliers producing sequential signals, and combinations thereof. Different characteristics of the electromagnetic radiation may be detected including: emission wavelength, emission intensity, burst size, burst duration, fluorescence polarization, and any combination thereof.

The detection process can also be automated, wherein the apparatus comprises an automated detector, such as a laser scanning microscope.

In some embodiments, the apparatus as disclosed can comprise at least one detector; in other embodiments, the apparatus can comprise at least two detectors, and each detector can be chosen and configured to detect light energy at the specific wavelength range emitted by a label. For example, two separate detectors can be used to detect particles that have been tagged with different labels, which upon excitation with an electromagnetic source, will emit photons with energy in different spectra.

Kits

In another aspect, the present invention is directed to kits for detecting an analyte. In exemplary embodiment, the kits include a micropore array of plurality of longitudinally fused capillaries have a diameter of about 1 micrometer to about 500 micrometers. In certain embodiments, the capillaries minimize light or EM radiation transmission between capillaries. The kits may also include particles that are able to move within a sample liquid when subjected to motive force, such as magnetic particles. These particles may include a binding partner for the analyte or other sample component. In certain embodiments, the kits include magnetic particles that have been functionalized with a binding partner for the analyte. In addition, the kit can optionally include one or more labels capable of emitting electromagnetic radiation, wherein the labels may be conjugated to a binding partner for the analyte or other sample component. The kits may also include second, third, or fourth, etc. set of particles that are functionalized to bind second, third, or fourth, etc. analytes in the sample, or to provide for the normalization of the sample components between micropores of the array. Stabilizers (e.g., antioxidants) to prevent degradation of the reagents by light or other adverse conditions may also be part of the kits. In other embodiments, the kits contain antibodies specific for a protein expressed from a gene of interest, in addition to detection reagents and buffers. In other embodiments, the kits contain reagents specific for the detection of mRNA or cDNA (e.g., oligonucleotide probes or primers).

The kits may optionally include instructional materials containing directions (i.e., protocols) providing for the use of the micro-pore array in the detection of various biological compounds that are secreted from a biological cell. While the instructional materials typically include written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In other embodiments, the present invention provides kits for the detection, identification, and/or characterization of proteins and/or nucleic acids. In some embodiments, the kits contain antibodies specific for an analyte, such as a protein of interest, in addition to detection reagents and buffers. In other embodiments, the kits contain reagents specific for the detection of mRNA or cDNA (e.g., oligonucleotide probes or primers). In various embodiments, the kits contain all of the components necessary to perform a detection assay, including all controls, directions for performing assays, and any necessary software for analysis and presentation of results Biological Recognition Assays Although it is not necessary to understand the mechanism of an invention, it is believed that the arrays described above comprise micro-pores having sufficient volume to incubate the cells for between 0-240 hours, such that compounds of interest are secreted from the cells and bind to the binding partner. Consequently, a plurality of biological recognition assays may be performed either within, or between, each of the micro-pores. For example, one such recognition assay may comprise antigen-antibody binding.

In one embodiment, the present invention contemplates a method for antigen-antibody binding comprising incubating a plurality of cells at 37° C. for 1-24 hours such that each cell produces antibodies and secretes the antibodies into the micro-pore. In one embodiment, the antibody is a recombinant antibody. In one embodiment, the antibody is a monoclonal antibody. In one embodiment, at least one of the cells produces more than one antibody. Although it is not necessary to understand the mechanism of an invention, it is believed that because of the micropore architecture, this incubation has reduced evaporation losses due to the very narrow inlets (thus small exposed surface area) and the extreme length of the pores. In one embodiment, the antibody secretion is stimulated by an induction agent. In one embodiment, the induction agent comprises IPTG. See, FIG. 3.

Therapeutic Drug Discovery

In one embodiment, the present invention contemplates a method comprising identifying new therapeutic drugs. For example, particles may be coated with a drug binding partner known to be involved in a disease condition (i.e., for example, a biological receptor and/or enzyme). A plurality of cells secreting various compounds suspected of having affinity for the binding partner is then screened using the very high-density micro-pore array. The micro-pores containing the particles attached to binding partner-compound complexes having the highest affinity are selected for future development.

Diagnostic Antibody Discovery

In one embodiment, the present invention contemplates a method comprising identifying diagnostic antibodies. For example, particles may be coated with a binding partner known to be involved in a disease condition (i.e., for example, an antigen and/or epitope). A plurality of cells secreting various antibodies suspected of having affinity for the binding partner is then screened using the very high-density micro-pore array. The micro-pores containing particles the binding partner-antibody complexes having the highest affinity are selected for future development.

Protein-Protein Interaction Studies

In one embodiment, the present invention contemplates a method comprising identifying protein-protein interactions. For example, particles may be coated with a binding partner known to be involved in a disease condition (i.e., for example, a protein and/or peptide). A plurality of cells secreting various proteins and/or peptides suspected of having affinity for the binding partner is then screened using the very high-density micro-pore array. The micro-pores containing particles with immobilized binding partner-protein or peptide complexes having the highest affinity are selected for future development.

Protein-Nucleic Acid Interaction Studies

In one embodiment, the present invention contemplates a method comprising identifying protein-nucleic acid interactions. For example, particles may be coated with a binding partner known to be involved in a disease condition (i.e., for example, a deoxyribonucleic acid and/or a ribonucleic acid and/or a SOMAmer and/or a Aptamer). A plurality of cells secreting various proteins and/or peptides suspected of having affinity for the binding partner is then screened using the very high-density micro-pore array. The micro-pores containing particles with immobilized binding partner-nucleic acid complexes having the highest affinity are selected for future development.

Protein-Carbohydrate Interaction Studies

In one embodiment, the present invention contemplates a method comprising identifying protein-carbohydrate interactions. For example, particles may be coated with a binding partner known to be involved in a disease condition (i.e., for example, an oligosaccharide, and liposaccharide, or a proteosaccharide). A plurality of cells secreting various lectins, proteins and/or peptides suspected of having affinity for the binding partner is then screened using the very high-density micro-pore array. The micro-pores containing particles with immobilized binding partner-carbohydrate complexes having the highest affinity are selected for future development.

Detection of Protein

Disclosed herein is the use of a highly sensitive system to identify a protein analyte from a heterologous population of biological elements. The disclosed methods and system provide a novel and important tool for protein engineering. In particular, the uses disclosed herein should lead to a significant reduction in time of new antibody discovery, from 14 days to 1-2 days. In other embodiments, gene expression may be detected by measuring the expression of a protein or polypeptide.

In one embodiment, the disclosed method is used to detect a protein analyte. The detection of a particular analyte protein can be performed directly in the pores of the array. Images are taken after the particles are accumulated at the detection surface of the pore, such that the background signal is inhibited.

The biochemical sensing can be done using standard detection techniques including a sandwich immunoassay or similar binding or hybridizing reactions. In conjunction with the magnetic particle the media is loaded with secondary antibodies that are optically labelled (e.g., attached to fluorochromes).

The secondary antibodies bind to the particle if the target protein produced by the elements binds to the antigen that is attached to the particle surface (See FIG. 3A). To maximize the binding capability of the target protein to the antibodies, the magnetic particles are kept in suspension by periodically (for example, approximately every 20 min.) exposing them to a magnetic field such that the particles are circulated throughout the liquid contained in the sample volume.

Detection of Nucleic Acids

In one embodiment, the analyte is a nucleic acid. For example, DNA or mRNA expression may be measured by any suitable method, For example, RNA expression is detected by enzymatic cleavage of specific structures (IN-VADER® assay, Third Wave Technologies; See, e.g., U.S. Pat. Nos. 5,846,717, 6,090,543; 6,001,567; 5,985,557; and 5,994,069; each of which is herein incorporated by reference). The INVADER® assay detects specific nucleic acid (e.g., RNA) sequences by using structure-specific enzymes to cleave a complex formed by the hybridization of overlapping oligonucleotide probes.

In still further embodiments, RNA (or corresponding cDNA) is detected by hybridization to an oligonucleotide probe. A variety of hybridization assays using a variety of technologies for hybridization and detection are available. For example, in some embodiments, TAQMAN® assay (PE Biosystems, Foster City, Calif; See, e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ® GOLD DNA polymerase. A probe consisting of an oligonucleotide with a 5-reporter dye (e.g., a fluorescent dye) and a 3'-quencher dye is included in the PCR reaction. During PCR, if the probe is bound to its target, the 5'-3' nucleolytic activity of the AMPLITAQ® GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

Detection of Cells

In another embodiment, the analyte is a biological cell. In one embodiment, the analyte is at least one biological cell.

The detection disclosed herein may be used to isolate any types of biological cells, including, but not limited to, cell lines that express or produce proteins, carbohydrates, enzymes, peptides, hormones, receptors; other cell lines that produce antibodies; genetically engineered cells; and/or activated cells. Moreover, the present invention may be used to screen for a variety of biological activities including, but not limited to, the expression of surface receptor proteins, enzyme production, and peptide production. Furthermore, the present invention may be used to screen a variety of test agents to determine the effect of the test agents on the desired biological activity. Other types of cells desired to be isolated and screened, other types of biological activity desired to be detected, and specific test agents to be screened will be readily appreciated by one of skill in the art.

In a particular embodiment, the biological cell is a transformed biological cell. Transformation of cells can occur by any well-known methods, using any well-known vectors, such as for example a plasmid or virus.

In one embodiment, the biological cell is a microbial, fungal, mammalian, insect or animal cell. In one embodiment, the microbial cell is a bacterial cell. In one embodiment, the bacterial cell is an *E. coli* cell.

In one embodiment, the animal cell includes a rare biochemical compound. In one embodiment, the rare biochemical compound is selected from the group comprising a protein, a peptide, a hormone, a nucleic acid, a carbohydrate.

In another embodiment, the biological cell produces and/or expresses a fluorescent protein. In yet another embodiment, the biological cell produces fluorescent protein (eg. GFP).

EXAMPLES

The following examples are offered to illustrate, but not to limit, the claimed invention.

Example 1: Magnetic Bead Signal Blocking

This example demonstrates the ability of the magnetic beads to inhibit the high background signal from labels in solution that are not bound to the particles.

A clean and dry 20 μm pore diameter array plate (J5022-19, Hamamatsu Photonics K. K.) was loaded with 10 μM Alexa 488 fluorochrome (Sigma Aldrich) as a label and 2.8 μm magnetic particles such that each pore receives both labels and magnetic particles. The fluorochrome label alone does not bind or associate with the magnetic bead particles.

The pores of the array are not exposed to any motive force prior to detection, so both the magnetic particles and the labels both remain in solution. Following incubation, this array comprising the magnetic particles and labels is subjected to EM radiation and the fluorescent emission from the label is imaged using a microscope. As expected, as shown in FIG. 5A, all of the pores show significant signal, for the unbound labels in solution have full exposure to the EM radiation. The fluorescent images were captured using a CCD camera. When the pixel count and intensity was quantified, the signal shows a pixel count at the appropriate intensity of about $4 \times 10^5$. Therefore, in the absence of particle accumulation, the unbound labels in solution will emit signal in nearly all of the pores regardless of their content.

Next, in the same array, the magnetic particles were accumulated to the detection surfaces of each reaction vessel of the array (e.g., meniscus in this example) by placing a 10 mm cubed neodymium magnet (B666, K&J Magnetics Inc.) at the bottom of the array (within 3 mm) for 60 seconds. After the particles have accumulated, another fluorescent image is captured of the same location. As shown in FIG. 5B, the image shows a striking decrease in pores with signal. Indeed, nearly all of the pores have lost or reduced their signal. When the signal is quantified, the signal at the appropriate intensity in the accumulated array drops to zero. The signal from the unbound labels is inhibited by the magnetic beads and only the basal autofluorescence from the array remains. Surprisingly, the accumulation of particles at the detection surface of the sample represents a novel strategy for eliminating background signal from unbound labels each pore.

Example 2: Assay Preparation

This example provides a representative assay system for detecting the presence or absence of an analyte in an array. The final screening design will, of course, depend on many factors specific to the experiment and its objectives.

The *E. coli* strain Imp4213, which contains a plasmid expressing GFP, was used in this assay. Approximately 1.0 to 10 million GFP-expressing bacterial cells were added into 5 mL of Luria broth (LB) media with 25 µg/ml kanamycin (KAN) and expanded on a shaker (200 RPM) at 37° C. for approximately 3 hours until the bacteria entered the exponential growth phase, and then were prepared for plating.

The particles used in this example are magnetic beads. Specifically, for these examples, the particles used were 2.8 µm diameter magnetic beads (Dynabeads) coupled to a either streptavidin (Part No. 112-05D, Invitrogen, Carlsbad, CA) or oligo(dt)$_{25}$ ligands (Part No. 610-05, Invitrogen, Carlsbad, CA). The magnetic beads were incubated with a biotinylated rabbit anti-GFP antibody (A10259, Invitrogen, Carlsbad, CA) for about 30 minutes, which bound the anti-GFP antibody to the magnetic beads via the biotin-streptavidin interaction. Therefore the anti-GFP magnetic beads were generated.

In this example, before the cells are added to the array, the cells are supplemented with the magnetic beads and labels. The magnetic beads (either anti-GFP beads to detect analyte or oligo(dt)$_{25}$ beads as a negative control) were added to a concentration of 30 mg/ml. The label is generated by combining 15 µg/ml biotinylated rabbit anti-GFP (A10259, Invitrogen, Carlsbad, CA) with fluorophore Atto 590 conjugated to streptavidin (40709-1MG-F, Sigma Aldrich), which forms a fluorescently-labeled anti-GFP antibody. For this assay design, any fluorophore label could be used, as long as it does not emit EM radiation around the same wavelength as GFP.

The cells were added to a clean and dry 20 µm pore diameter array plate (J5022-19, Hamamatsu Photonics K. K.) by placing a drop onto the array and spreading the analysis mixture on to the array plate surface to approximately 1 µl/mm$^2$ (FIG. 3). The mixture is spontaneously distributed into the pores through the hydrophilic pore surface.

Once the sample is distributed, the array plate is placed on a holder such that the pore array plate is 80 µl above the capture surface (Sylgard® 184 Silicone Elastomer Kit, Dow Corning). The holder is composed of a glass slide (12-550-14, Fisher Scientific) with a 250 µm thick capture surface, two 80 µm adhesive tape spacers on either side of the capture surface. Once the pore array is placed on the holder, the upper side of the array is sealed with plastic wrap (22-305654, Fisher Scientific). The full setup is placed into a 100 mm petri dish with two 10 mm deionized water-wet tissue paper spheres for humidity saturation. The dish is sealed with parafilm and allowed to incubate at 37° C. for 19 hours.

To select for pores with the analyte, the magnetic beads are accumulated at the bottom surface of the pore array by placing a 10 mm cubed neodymium magnet (B666, K&J Magnetics Inc.) at the bottom of the array (within 3 mm) for 60 seconds. The array on the holder is then loaded into an Arcturus Laser Capture Microdissection System (Model: Veritas, Applied Biosystems, USA) to facilitate detection.

To detect fluorescence of pores containing analyte, the immunoassay results are scanned by reading the bottom surface fluorescence of the pore array plate with a microscope comprising a 20× objective and a 594 nm excitation 630 nm emission fluorescent cube. Image capture was performed using a CCD camera.

Example 3: Detection of Analyte in Array

This example illustrates that a protein binding and detection assay can be performed directly in the pores using the methods disclosed herein. In this embodiment, the assay system is set up according to the steps described in Example 2.

The first array contains pores comprising the anti-GFP magnetic particles and the anti-GFP labels generated as described in Example 2. After incubation, the array is exposed to a magnetic force, as described, moving the particles to the detection surface of the sample, which in this example is the meniscus of each vessel of the array. An image of this array is captured. The anti-GFP magnetic particles bound to the target protein (GFP), which is also bound by the anti-GFP label. The magnetic forces move the labeled particles to the detection surface, therefore concentrating the signal-emitting labels at the detection surface, and inhibiting the unbound labels from transmitting EM radiation to the detector or microscope. A schematic diagram of this interaction within the pore is shown in FIG. 1B.

The second array contains particles that are bound to ligand oligo-dT rather than streptavidin. Without streptavidin, the biotin conjugated to the anti-GFP antibody does not interact or bind with the magnetic particles. Therefore both the magnetic particles, anti-GFP antibodies, and anti-GFP labels remain in solution. After incubation, the array is exposed to magnetic force, moving the particles to the detection surface. The array is imaged following EM radiation exposure. Since the oligo-dT magnetic particles are not bound to any label, they accumulate to the detection surface and inhibit the EM radiation from reaching the label in solution. The particles also can be used to inhibit the detector from detecting the EM radiation emitted from the labels unbound to the magnetic particles. If the amount of fluorescence from each array is quantified, the emission from the specific anti-GFP magnetic beads is substantially higher than the negative control oligo(dt) beads.

Therefore, this experiment shows that the magnetic bead inhibiting methods as disclosed can select analyte-containing pores by specific inhibiting of pore signal.

Example 3: Single Cell Specific Detection

The following example demonstrates the specificity of the disclosed methods for detecting analytes at the single cell level.

In this embodiment, the assay system is set up according to the steps described in Example 2, except that before the cells are plated, the bacterial cells were diluted to 300 cells per microliter, which was calculated to result in approximately 0.1 cell per pore on the array plate with pores having a 20 micrometer diameter. When added to the array, this dilution will yield up to a single bacterial cell in most pores.

The anti-GFP streptavidin beads and anti-GFP label were added to the first array as described. The corresponding signal seen when EM radiation is exposed to the array following magnetic bead accumulation is shown in FIG. 7A. Many cells are signal-producing, which represents fluorescent signal from streptavidin magnetic beads that are bound to biotinylated anti-GFP antibody via streptavidin-biotin linkage. After applying magnetic force, only cells that express the analyte target protein (GFP) and therefore bind the beads to the label provide positive signal. However, also observed with single cell dilutions are pores with reduced or absent signal. These pores most likely lack any GFP-producing cells and/or contain bacterial cells that no longer express GFP. Therefore no label is bound to magnetic particle, and upon application of magnetic force, the magnetic particles inhibit the detection surface.

Accordingly, the other array comprising oligo(dt)$_{25}$ beads depicts very little fluorescent signal from pores, as shown in FIG. 7B. In this array, there is no anti-GFP antibody bound to the beads, and therefore no label bound to the beads. After applying magnetic force, none of the cells that express the analyte target protein (GFP) will provide signal, since the magnetic beads have accumulated to the detection surface without a label. In this setup, the EM radiation from the EM source cannot reach the unbound label in solution for these pores. Therefore, no signal is observed in this array. The magnetic beads could also be accumulated between the sample and the detector to inhibit emission from the label to the detector.

Example 4: Detection does not Require Lysis of Cells

This example shows that performing a sandwich immunoassay with beads in the array does not require cell lysis for analyte detection.

In these embodiments, the arrays were prepared as described in the previous examples with the two positive control arrays containing magnetic beads linked to anti-GFP antibody. The cells of one positive control array were lysed using sonication for 1.5 minutes at 5 watts prior to detection using a Misonix 4000 with Microplate horn, while the other positive control array was not lysed.

Figure 8:
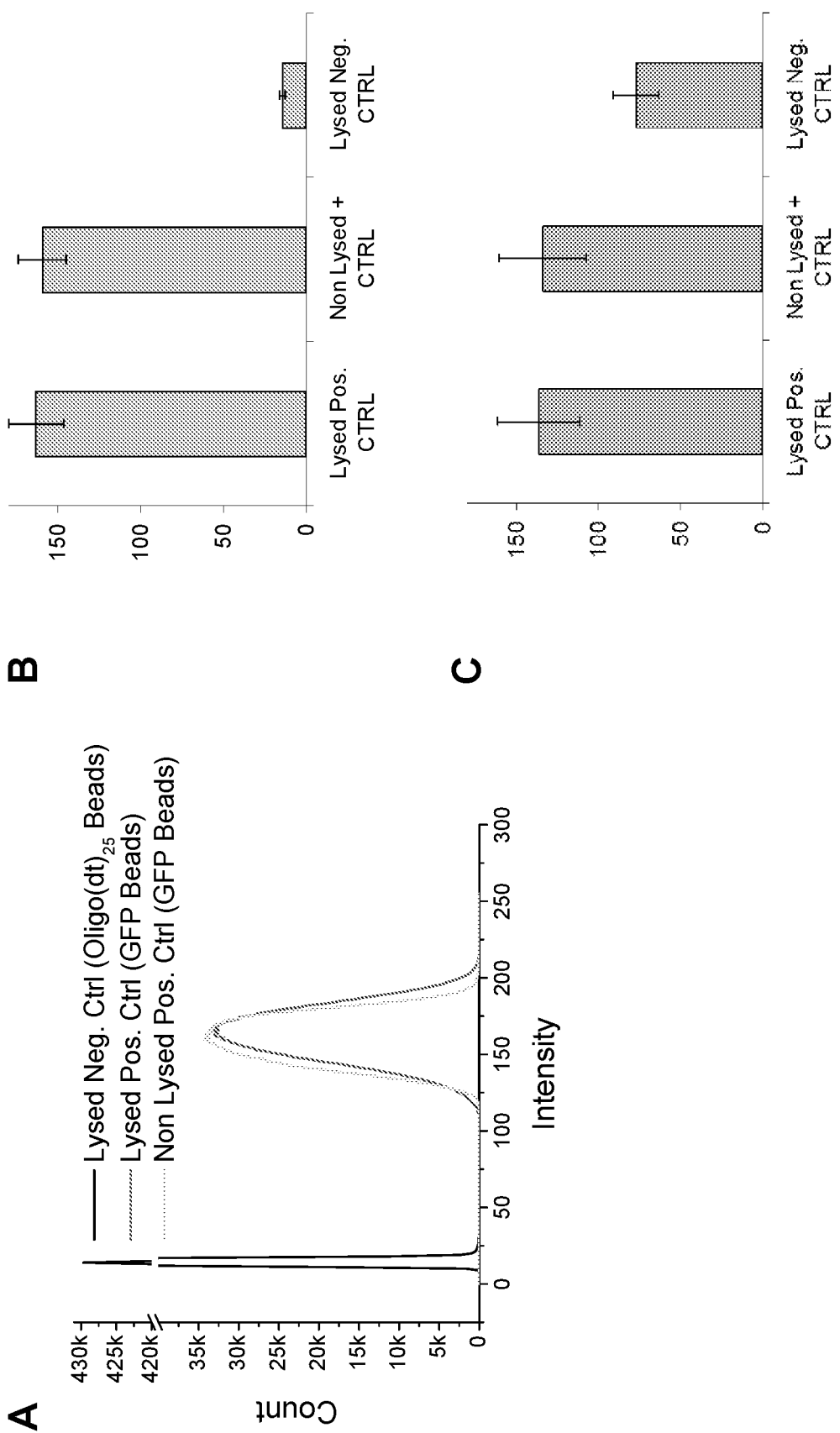
FIG. 8 demonstrates that the methods disclosed herein do not require cell lysis for analyte detection. In these embodiments, the arrays were loaded with E. coli cells expressing recombinant protein GFP. Each well also contains fluorescent labels (Atto 590), which is also linked to a rabbit anti-GFP antibody. The two positive control wells contain magnetic beads linked to anti-GFP antibody, but the cells of one array were lysed using sonication prior to detection. The negative control arrays were lysed using sonication, and contain Oligo-dT beads, which universally inhibit the signal from all pores in the array

The negative control array contains Oligo-dT beads, which earlier examples have shown inhibit the signal from all pores in this array system. The negative control array was lysed using the same sonication conditions as the positive control array. The results indicate (see FIG. 8A-C) that both of the positive control arrays have similar signal levels regardless of cell lysis (sonication) step, based on the quantification of pixel count. Further, the lysis step did not remove the selectivity of the particle inhibiting, for the negative control beads still remain far below the positive control levels. FIGS. 8A and 8B. This suggests that for certain expression mechanisms cell lysis is not required to detect analytes using the methods described herein.

Example 5: Extraction and Recovery of Cells

The following example demonstrates the display and independent recovery of a single target among billions of target cells.

In this example, the cells, beads, labels, and arrays are prepared as described in Example 2. After identification of one or more pores containing analyte, extraction of the solution in the single pore is desired.

As described and depicted in FIG. 9, the array is placed on a holder such that the pore array is about 80 micrometers above the capture surface. The holder is composed of a glass slide (12-550-14, Fisher Scientific) with a 250 µm thick capture surface, two 80 µm adhesive tape spacers on either side of the capture surface. Once the pore array is placed on the holder the upper side of the array is sealed with plastic wrap (22-305654, Fisher Scientific).

For recovery, a pore of interest is selected, such as a high intensity pore. The pore is then extracted by focusing a 349 µm solid state UV laser at 20 to 30 percent intensity power and emitting a 20 microJoule pulse. The cells extracted from the targeted pore can then be located on the capture surface, as shown in FIG. 9.

After extraction, the holder and the array are then removed from the Arcturus Laser Capture Microdissection System and the capture surface containing the extracted cells is placed into 5 mL LB plus 25 µg/ml KAN media and incubated on a shaker at 37° C. for 19 hours to expand the extracted cells. These cells, which express the protein of interest, are then ready for any type of scale-up protein production and/or further processing.

Example 6: Modifying Reagent Concentration in Pores of the Array

The following example demonstrates that reagents and other molecules, such as magnetic beads, can be added to the array after it is loaded without disturbing the cells within the array.

Figure 10:
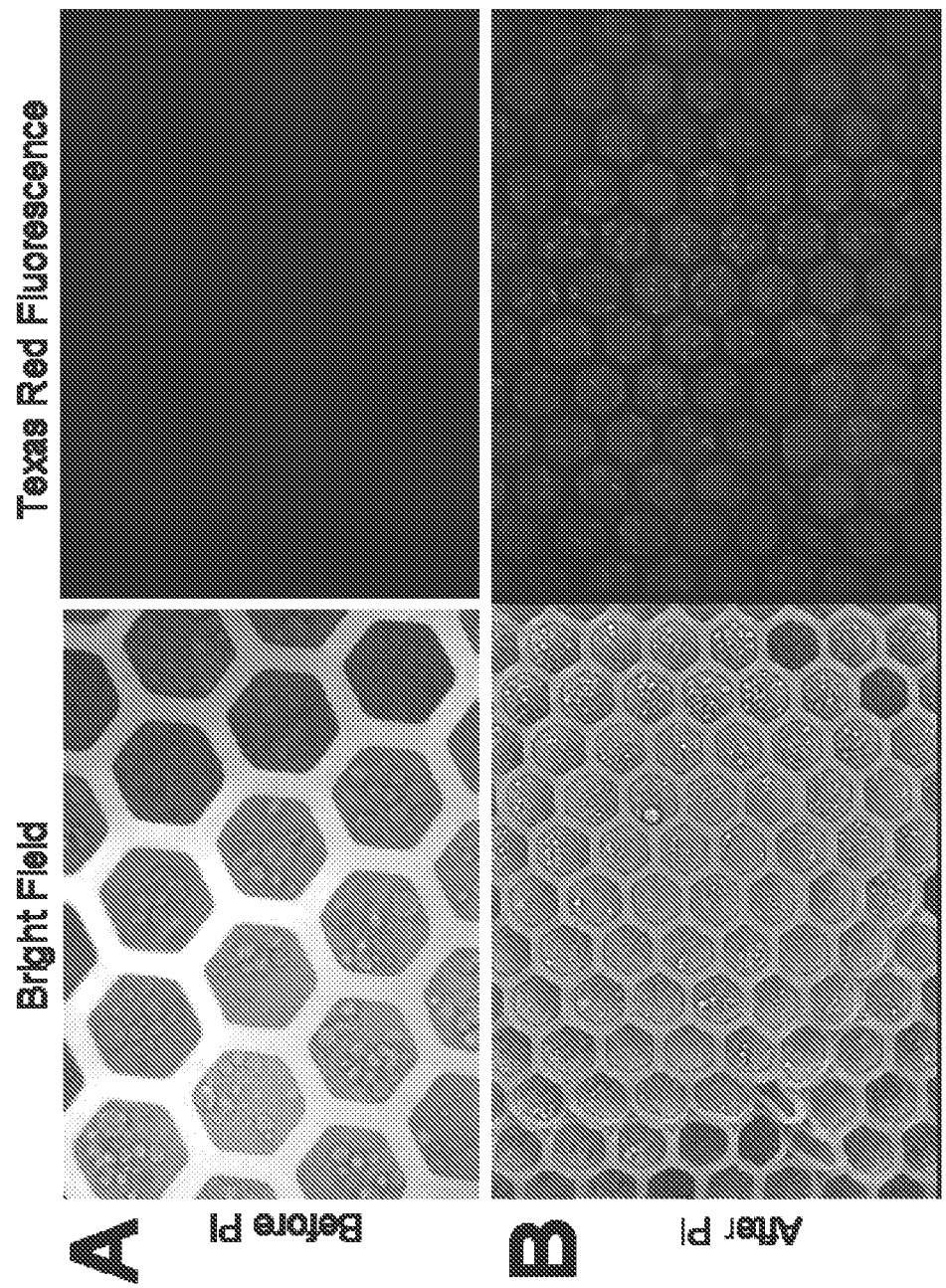
FIG. 10 demonstrates that reagents, particles, or other molecules can be added or subtracted from the array containing cells without disturbing the cells. Propidium iodide (PI) was loaded into the micropore array without disturbing the preloaded HEK 293 cells. Part A: Before PI loading with minimal background signal. Part B: After loading PI that has intercalated into the nucleuses of the non-viable HEK 293 cells.

In this embodiment, Freestyle 293 Media containing Human Embryonic Kidney 293 (HEK 293) cells was added at a concentration of 2,500 cells/µL into a micro-pore array with a pore diameter of 100 µm. This loaded about 20 cells per pore, with a cell viability of about 50%. The cells were first imaged with a fluorescent microscope at 10× using a Texas Red filter cube to measure any background fluorescence in that channel (FIG. 10A). Next, a 50 µL drop of Freestyle Media with 2 µg/mL propidium iodide (PI) was placed on top of the micropore array. At 660 Daltons, PI is a relatively small molecule and diffuses about 400 µm in 60 seconds in an aqueous solution at room temperature. Because the micropores are approximately 1 mm long, the loaded cells at the bottom of the micropores should be exposed to PI molecules after about 5 minutes. This was confirmed by detecting the intercalation of the PI molecules with the DNA in the nucleuses of the non-viable HEK 293 cells as shown in FIG. 10B.

Additional Embodiments: The following additional embodiments are non-limiting and presented here to further exemplify various aspects of the disclosure.

An apparatus for detecting a target biological element comprising:
   an array of micropores having an internal diameter of about 1 micrometer to about 500 micrometers,
   a magnetic source that applies a magnetic field to the array,
   an electromagnetic radiation source for applying electromagnetic radiation to the array, and
   a detector that receives electromagnetic radiation from the array and identifies the location of at least one micropore emitting the radiation.

The apparatus further comprises magnetic particles comprising a binding partner in each micropore of the array.

The apparatus further comprises an energy source that focuses energy on the micropores that emit electromagnetic radiation.

The micropores of the apparatus are not translucent.

The micropores are coated with a material that prevents light transmission between the pores.

A kit for detecting an analyte, comprising: a micropore array comprising a plurality of longitudinally fused fibers having a diameter of about 1 micrometer to about 500 micrometers, and magnetic particles comprising a binding partner for the analyte.

The micropores are not translucent.

The micropores are coated with a material that prevents light transmission between the pores.

Although various specific embodiments of the present invention have been described herein, it is to be understood that the invention is not limited to those precise embodiments and that various changes or modifications can be affected therein by one skilled in the art without departing from the scope and spirit of the invention.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention.

It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32, etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

The disclosures of all references and publications cited herein are expressly incorporated by reference in their entireties to the same extent as if each were incorporated by reference individually.

The invention claimed is:

1. A method for detecting an analyte in a sample, comprising:
   distributing the sample into an array of receptacles, wherein the array of receptacles comprises a microcavity comprising a plurality of longitudinally fused capillaries each having a diameter of about 1 to about 500 micrometers;
   adding to the array, first particles and a first label that emits electromagnetic radiation, wherein the first label is bound to the first particles or the first label becomes bound to the first particles as a result of the presence or absence of the analyte in the sample,
   accumulating the first particles at a first detection surface in each of the receptacles to inhibit the transmission of electromagnetic radiation into and out of the sample through the first detection surface, and
   detecting the presence or amount of electromagnetic radiation emitted from the first particles at the first detection surface of the receptacles.

2. The method of claim 1, wherein the first detection surface comprises a first meniscus of the sample.

3. The method of claim 1, wherein the first label is released from the particle as a result of the presence or absence of the analyte in the sample.

4. The method of claim 1, wherein the first particles accumulate at the first detection surface as a result of a force applied to the sample, wherein the force is selected from the group consisting of gravitational, magnetic, electrical, centrifugal, convective and acoustic.

5. The method of claim 2, further comprising mixing the sample by applying a magnetic field to move the first particles within the sample, wherein the first particles are magnetic.

6. The method of claim 1, further comprising:
   adding to the array a second label that emits electromagnetic radiation and second particles that are different from the first particles based upon at least one of the following properties: shape, size, density, magnetic permittivity, charge, and optical coating, wherein the second label is bound to the second particles or the second label becomes bound to the second particles as a result of the presence or absence of a second analyte in the sample;
   accumulating the second particles at a second detection surface in each of the receptacles to inhibit the transmission of electromagnetic radiation into and out of the sample through the second detection surface; and
   detecting the presence or amount of electromagnetic radiation emitted from the second particles at the second detection surface of the receptacles.

7. The method of claim 6, wherein the first particles accumulate at the first detection surface as a result of a first force and the second particles accumulate at the second detection surface as a result of second force, wherein the first force and the second force are independently selected from the group consisting of gravitational, magnetic, electrical, centrifugal, convective and acoustic force, and wherein the first force and the second force are applied to the sample either simultaneously or sequentially.

8. The method of claim 1, further comprising:
   adding to the array a second label that emits electromagnetic radiation and second particles that are different from the first particles based upon at least one of the following properties: shape, size, density, magnetic permittivity, charge, and optical coating, wherein the second label is bound to the second particles or the second label becomes bound to the second particles as a result of the presence or absence of a second analyte in the sample;
   accumulating the second particles at the first detection surface in each of the receptacles to inhibit the transmission of electromagnetic radiation into and out of the sample through the first detection surface, wherein the first particles accumulate at the first detection surface as a result of a first force and the second particles accumulate at the first detection surface as a result of second force, wherein the first force and the second force are independently selected from the group consisting of gravitational, magnetic, electrical, centrifugal, convective and acoustic force; and
   detecting the presence or amount of electromagnetic radiation emitted from the first receptacles and/or the second receptacles at the first detection surface of the receptacles.

9. The method of claim 1, wherein the array comprises between about 300 and 64,000,000 capillaries per square centimeter of the array.

10. The method of claim 1, wherein the sidewalls of the microcavity of each of receptacles are not translucent.

11. The method of claim 1, wherein the sample comprises biological element.

12. The method of claim 11, wherein the biological element is an organism, cell, protein, nucleic acid, lipid, saccharide, metabolite, or small molecule.

13. The method of claim 12, wherein the biological element is a cell.

14. The method of claim 1, wherein the sample is added to the array at a concentration that is intended to introduce no more than a single biological element in each receptacle.

15. The method of claim 1, wherein reagents are added to the array by introducing fluids comprising the reagents to the top of the array.

16. The method of claim 6, wherein the detecting the presence or amount of electromagnetic radiation emitted from the first particles and the second particles is either simultaneously or sequentially.

17. The method of claim 8, wherein the detecting the presence or amount of electromagnetic radiation emitted from the first particles and the second particles is either simultaneously or sequentially.

18. The method of claim 8, wherein the first force and the second force are applied to the sample sequentially.

* * * * *